(12) United States Patent
Sudre et al.

(10) Patent No.: US 11,024,100 B2
(45) Date of Patent: Jun. 1, 2021

(54) METHOD AND APPARATUS FOR TRANSFORMING PHYSICAL MEASUREMENT DATA OF A BIOLOGICAL ORGAN

(71) Applicant: UCL Business LTD, London (GB)

(72) Inventors: Carole Sudre, London (GB); M Jorge Cardoso, London (GB); Sebastien Ourselin, London (GB); Jonathan Rohrer, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/323,608

(22) PCT Filed: Aug. 10, 2017

(86) PCT No.: PCT/GB2017/052360
§ 371 (c)(1),
(2) Date: Apr. 24, 2019

(87) PCT Pub. No.: WO2018/029479
PCT Pub. Date: Feb. 15, 2018

(65) Prior Publication Data
US 2019/0172270 A1    Jun. 6, 2019

(30) Foreign Application Priority Data

Aug. 10, 2016 (GB) ...................................... 1613733

(51) Int. Cl.
*G06T 19/20* (2011.01)
*G06F 19/00* (2018.01)
(Continued)

(52) U.S. Cl.
CPC ............ *G06T 19/20* (2013.01); *G06F 19/321* (2013.01); *G06T 15/08* (2013.01); *G06T 17/10* (2013.01);
(Continued)

(58) Field of Classification Search
None
See application file for complete search history.

(56) References Cited

U.S. PATENT DOCUMENTS

| | | | |
|---|---|---|---|
| 6,347,318 B1 * | 2/2002 | Rokicki | G06F 16/9027 707/752 |
| 2010/0201687 A1 | 8/2010 | Breeuwer et al. | |

(Continued)

FOREIGN PATENT DOCUMENTS

| | | |
|---|---|---|
| TW | 201332518 A | 8/2013 |
| WO | 2004003851 A2 | 1/2004 |
| WO | 2015150320 A1 | 10/2015 |

OTHER PUBLICATIONS

International Search Report for Int'l Application No. PCT/GB2017/052360, titled: A Method and Apparatus for Transforming Physical Measurement Data of a Biological Organ, dated Oct. 25, 2017.
(Continued)

*Primary Examiner* — Frank S Chen
(74) *Attorney, Agent, or Firm* — Hamilton, Brook, Smith & Reynolds, P.C.

(57) ABSTRACT

An apparatus is configured for performing a computer-implemented method comprising: receiving data comprising physical measurements of a biological organ across a three-dimensional (3D) volume, the organ having a hierarchical structure of elements with multiple levels; transforming the physical measurement data into a two-dimensional (2D) data representation having first and second axes, wherein the first axis corresponds to location of an element a spatial path through the three-dimensional volume based on the hierarchical structure of the organ, and the second axis corresponds to descending successive levels through said hierarchical structure; and outputting the two-dimensional data representation to an apparatus for display.

20 Claims, 26 Drawing Sheets

(51) Int. Cl.
 G16H 50/50 (2018.01)
 G06T 15/08 (2011.01)
 G06T 17/10 (2006.01)
(52) U.S. Cl.
 CPC ......... *G16H 50/50* (2018.01); *G06T 2210/41* (2013.01)

(56) References Cited

U.S. PATENT DOCUMENTS

| 2013/0113816 | A1* | 5/2013 | Sudarsky | G06T 11/206 345/589 |
| 2015/0080753 | A1* | 3/2015 | Miyazaki | G16H 40/63 600/544 |
| 2018/0146910 | A1* | 5/2018 | De Vries | A61B 5/1123 |

OTHER PUBLICATIONS

Notification Concerning Transmittal of Copy of International Preliminary Report on Patentability dated Feb. 21, 2019 re International Application No. PCT/GB2017/052360 entitled "A Method and Apparatus for Transforming Physical Measurement Data of a Biological Organ".
Anonymous: "Baobab—Ringschart," XP055418204, Aug. 28, 2015 (http://web.archive.org/web/20150828065445/http://www.marzocca.net/linux/baobab/baobab-ringschart.html—retrieved Oct. 23, 2017).
Asman, A. J., et al., "Non-local statistical label fusion for multi-atlas segmentation," Medical Image Analysis, 17(2), 194-208 (2013).
Cerqueira, M. D., "Standardized Myocardial Segmentation and Nomenclature for Tomographic Imaging of the Heart: A Statement for Healthcare Professionals From the Cardiac Imaging Committee of the Council on Clinical Cardiology of the American Heart Association," Circulation, 105(4), 539-542 (Jan. 29, 2002).
Kim, K. W., M., et al., "Classification of white matter lesions on magnetic resonance imaging in the elderly," Biological Psychiatry, 64(4), 273-280. (2008).
Liu, S. X., "Symmetry and asymmetry analysis and its implications to computer-aided diagnosis: A review of the literature," Journal of Biomedical Informatics, 42(6), 1056-64. (2009).
Schiffmann, R., et al., "Invited article: an MRI-based approach to the diagnosis of white matter disorders," Neurology, 12(8), 750-9. (2009).
Snowden, J. et al., "Frontotemporal lobar degeneration: clinical and pathological relationships," Acta Neuropathologica, 114(1), 31-8. (2007).
Volkau, I., et al., "Quantitative analysis of brain asymmetry by using the divergence measure: normal-pathological brain discrimination," Academic Radiology, 13(6), 752-8. (2006).
Winston, G. P., et al., "Automated hippocampal segmentation in patients with epilepsy: available free on line," Epilepsia, 54(12), 2166-73. (2013).

* cited by examiner 1. basal anterior
2. basal anteroseptal
3. basal inferoseptal
4. basal inferior
5. basal inferolateral
6. basal anterolateral
7. mid anterior
8. mid anteroseptal
9. mid inferoseptal
10. mid inferior
11. mid inferolateral
12. mid anterolateral
13. apical anterior
14. apical septal
15. apical inferior
16. apical lateral
17. apex Left Hippocampus

METHOD AND APPARATUS FOR TRANSFORMING PHYSICAL MEASUREMENT DATA OF A BIOLOGICAL ORGAN

This application is the U.S. National Stage of International Application No. PCT/GB2017/052360, filed Aug. 10, 2017, which designates the U.S., published in English, and claims priority under 35 U.S.C. § 119 or 365(c) to Great Britain Application No. 1613733.3, filed Aug. 10, 2016. The entire teachings of the above applications are incorporated herein by reference.

FIELD OF THE INVENTION

The present invention relates to transforming physical measurement data of a biological organ obtained across a three-dimensional volume, for example to support display on a two-dimensional screen or similar apparatus.

BACKGROUND

Medical professionals make use of a number of tools to help diagnose illnesses, plan medical/surgical treatment and so on. For example, imaging devices (CT, MRI) and other systems may be used to obtain physical measurements across a three-dimensional (3D) volume of a biological organ. These physical measurements may be acquired from one or more properties (e.g. intensity, timing, spectral distribution) of a signal from each location in the volume, which may then be used to determine physical parameters such as a concentration of particular chemicals, etc. at the relevant locations. In the present context, the term physical measurement data will be used to denote both the original signal properties, and/or any physical parameters that may be derived from such signal properties. The physical measurement data are dependent on, i.e. vary with, location in the three-dimensional volume of the biological organ.

In many cases the physical measurement data are presented or displayed to a medical professional in a visual form. In some cases the displayed data may reflect the actual visual appearance of the biological organ as seen with the naked eye. In other cases the displayed data may represent information which is not directly visible to the naked eye, for example, because it represents radiation at other wavelengths or in other forms (e.g. infrared, X-ray, ultrasound), or because it represents some other physical properties, such as levels of electrical activity in the organ.

Human visual perception is predominantly based on two-dimensional (2D) surfaces. We have a line of sight in each direction, which terminates when it encounters a solid (opaque) surface. We understand the three-dimensional curvature and topology of such surfaces through binocular (depth) perception, and also through relative movement of the observer and the surface(s) being observed. Although we understand that physical objects have internal structure, for example, a mobile telephone may have incorporated within a battery, SIM card, printed circuit board (PCB), etc., our dominant impression of such physical objects is through their external appearance, such as their overall shape, surface colour and design, etc.

Display technology, for example, televisions, computer screens, etc., is also primarily surface-based—corresponding to the properties of human visual perception. We see a screen as a surface representing a single point of termination of each line of sight for a range of angles. There has been some development of three-dimensional televisions, movies, virtual reality (VR) systems, etc. However these systems are generally concerned with making the eye think that the distance along a given line of sight to a viewed surface is different from the true distance to the screen. In other words, such three-dimensional systems are still primarily surface-based, even though they now try to accommodate depth variations of the perceived surface.

This presents a problem in respect of three-dimensional measurement data such as that described above from medical imaging. Take, for example, a three-dimensional MRI scan of a biological organ, which is then to be viewed on a flat display screen. In some cases, the display may provide a depiction akin to normal sight, such that we see the external surface of the organ. In some cases, an organ displayed in this manner may be rotated, which helps us to build up an understanding of the surface contours in three-dimensional space. In other cases, the system may display a section through the biological organ, as if cut-through with a knife. It will be appreciated that all these different views represent only a subset of the underlying data set for the full three-dimensional volume. One common way of trying to provide a medical practitioner with additional information is to provide a combination of multiple such two-dimensional views (e.g. external views from different directions, sections from different planes, etc.). However, the resulting overall display may be rather complex, and can be difficult for a user to comprehend properly.

FIG. 1 provides one example of a display comprising multiple sections, in particular a representation of vascular burden provided as a schematic axial view from four (parallel) planes. One difficulty with this type of display is that a user may have to look at multiple images simultaneously (one for each section). Another problem is that the presentation of dimensions within the plane of the sections is clearly different from the presentation of the dimension normal to the plane.

FIG. 2 is another example of a display, this time showing quantified volumetric measures of different brain regions. This type of display might be rotated to give a clearer perception of the different brain regions, however, the ability to perform such a rotation may be limited to certain types of display device. In addition, the display of FIG. 2 is still primarily surface-based.

In other known alternatives, to help in the visualisation of the regions for which validation assessments are calculated, Asman et al. [1] highlight the corresponding region of an organ on a schematic axial view. When assessments are differentiated for the right and the left hemispheres, the results and corresponding vignettes are reported sequentially, as shown in FIG. 3.

The use of a 2D representation of a 3D organ to summarise quantified biomarkers is to date mostly seen in fields other than brain imaging, such as the reporting of the left myocardium (i.e., the heart). The adopted nomenclature dates back to 2002 [2] and is directly related to the cup-like nature of the myocardium and the choice of imaging planes. FIG. 4 depicts the accepted standard for left ventricle segmentation defined in [2]. In this regard, the left ventricle of the heart can be approximated as a cup-shape having an open end opposite a closed end. The closed end is represented by the apex (section 17 in FIG. 4) which is the tip of the ventricle. Each ring (basal, mid-cavity, and apical) signifies a slice through the heart progressing along a vertical axis of the cavity of the ventricle. In other words, one can imagine looking into a cup and seeing each slice of the cup as a progressively larger ring from the bottom, with the bottom surface of the cup representing the apex.

Apart from any regional division, the question of symmetry is often also important for the representation and assessment of biometric (volumetric) markers. Such symmetry is present (and biologically significant) in the brain with the right and left hemispheres (lobes), and in the functioning of the kidneys. On the other hand, such right-left symmetry is not generalizable to all organs—for example, lungs present a tri-lobar structure on the right while only two lobes are present on the left side. Nevertheless, when symmetry does exist, it usually represents an important tool for diagnosis. For example, in the literature, measures of left/right symmetry have been used to distinguish between normal and pathological brain configurations [4], [7]. Furthermore, asymmetrical atrophy has for instance been underlined as a potential way of distinguishing subtypes of fronto-temporal dementia [6], and neurodegeneration with associated aphasia has been shown to be reflected by an increased atrophy of the left hemisphere language area. In turn, symmetrical damage can be a useful sign for the diagnosis of toxic leukoencephalopathies [5] or help distinguish between subtypes of temporal lobe epilepsy. As an example, [8] illustrates the relevance of asymmetry measurements when evaluating hippocampal sclerosis in epilepsy.

Currently the type of diagram shown in FIG. 4 is used on a day-to-day basis in clinical products. It must however be noted that this diagram relies on 3D to 2D conformal mapping which is natural in the case of the heart. Conformal mapping preserves angles between regions or sections of a three-dimensional object mapped to a two-dimensional plane. Hence, such a technique cannot be applied to the brain as the brain is not homotopic to a disk.

SUMMARY

The invention is defined in the appended claims.

Various embodiments of the invention provide an apparatus and a computer-implemented method comprising: receiving data comprising physical measurements of a biological organ across a three-dimensional (3D) volume, the organ having a hierarchical structure of elements with multiple levels; transforming the physical measurement data into a two-dimensional (2D) data representation having first and second axes, wherein the first axis corresponds to location of an element along a spatial path through the three-dimensional volume based on the hierarchical structure of the organ, and the second axis corresponds to descending successive levels through said hierarchical structure; and outputting the two-dimensional data representation to an apparatus for display.

Many physical measurement (including imaging) systems for use in medicine and more generally biology are able to acquire three-dimensional data sets (or allow such 3D data sets to be generated). These 3D data reflect the 3D nature of biological organs. In particular, the 3D data set may indicate how physical parameters of medical or biological interest vary with location across the 3D volume of the biological organs.

However, 3D data sets can be relatively difficult to work with, firstly since display technology is usually inherently two-dimensional (computer screens, paper charts etc.), and also because human visual perception is primarily based on recognising the surfaces of objects, rather internal structure. It is therefore easier for a 3D data set to be displayed in 2D format (having regard to the available display systems), and also for such a 2D format to be appreciated and utilised by human practitioners. Many imaging systems provide such 2D format output from a 3D data set, typically using data projections (showing surfaces that would be visible from a particular location or slices (sections). These existing techniques are primarily geometrical in nature.

In contrast, the approach described herein generates a 2D data set representative of an original 3D data set by using a different transformation, one that is based more on anatomy (biology) than on geometry. It will be appreciated that any derivation of a 2D data set from an original 3D data set will involve some loss of information. However, it has been found that the anatomical basis of the present approach can help to preserve more useful information for clinicians, etc., than existing geometry-based approaches.

As noted above, the 2D data set provided by the present approach is based on a hierarchical structure for the organ (which may be derived from any appropriate anatomical, physiological and/or functional considerations). In particular, the 2D data set is configured based on first and second axes. The first axis represents a spatial path which typically defines a sequence or ordering of the elements at a given level of a hierarchical structure. This ordering can be selected to reflect, at least in part, the relative spatial arrangement of the elements—for example, so that elements which are adjacent in the ordering are also adjacent in the actual 3D volume of the biological ordering. The spatial path can further be selected to preserve a symmetry of the organ (such as left-right symmetry), which is often an important parameter for a practitioner. The second axis represents level in the hierarchy. Typically, each level of the hierarchy adopts the same spatial path for ordering the elements within that level (thereby providing consistency between different levels).

Overall, the approach described herein helps to provide a transformation of three-dimensional data of biological organs to a 2D representation that does not rely on a specific homotopic nature of the organ, while simultaneously encoding physical measurement data and three-dimensional relative spatial relationships and/or symmetry, thereby supporting easy and intuitive displays for practitioners.

BRIEF DESCRIPTION OF THE DRAWINGS

The invention is now described by way of example only with reference to the following drawings in which.

DETAILED DESCRIPTION

Figure 1:
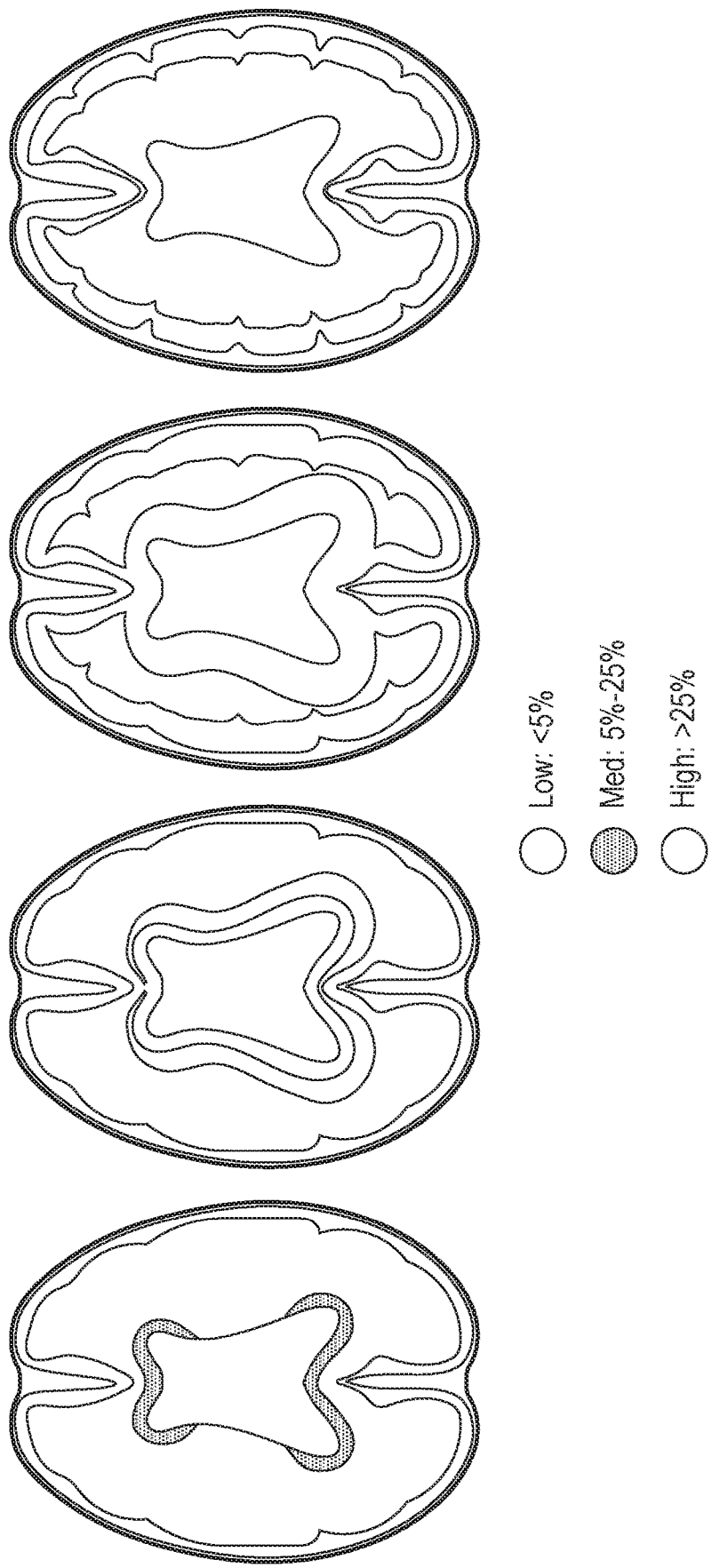
FIG. 1 is a known presentation of a set of multiple views of the brain.

Aspects and features of certain examples and embodiments of the present invention are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

In accordance with various embodiments of the invention, a computer-implemented method for generating a two-dimensional representation of three-dimensional physical measurement data is described with reference to FIG. 5. The method begins by receiving physical measurement data at step S1. This data comprises physical measurements of a biological organ, such as the brain, of a patient or subject across a three-dimensional (3D) volume. For example, the three-dimensional data may be obtained from three-dimensional images taken of the patient, such as computed tomography (CT) or magnetic resonance (MR) images; however, it should be appreciated that other conventional images or techniques, such as 3D ultrasound, measurements of radioactive tracers, etc. may also be used. Three-dimensional images can also be created (generated) from a series of individual 2D images, such as 2D ultrasound images, that are subsequently arranged or processed to create a three-dimensional representation of an organ.

In general, the three-dimensional measurement data is obtained as appropriate from the three-dimensional images. For example, a physical measurement value may be calculated for each pixel or group of pixels in the three-dimensional image and attributed to a three-dimensional coordinate assigned to a point, e.g., the middle, of the pixel/pixel group. From this, it should be understood that a data cloud of measurement points is realised with each measurement point having a position in the three-dimensional space and being assigned a physical measurement. In other situations, the three-dimensional data might be obtained by performing measurements at discrete locations with respect to the organ. For example, a probe which is moved relative to the organ might be used to measure one or more physical properties at a number of positions. Each measurement point is therefore directly indicative of the value of the physical measurement made at that point. In a similar way, a three-dimensional data cloud can be realised.

The three-dimensional physical measurement data may provide an indication of a physical parameter associated with the organ. For example, the parameter may be a measure of haemorrhaging at that location, which may be expressed as a percentage. Thus, the three-dimensional physical measurement data comprises, in this example, a number of points over the three-dimensional volume of the organ, each representing a percentage of haemorrhaging at that point. However, it will be appreciated that the present approach is not dependent upon the specific type, format, and properties of the three-dimensional physical measurement data.

Figure 5:
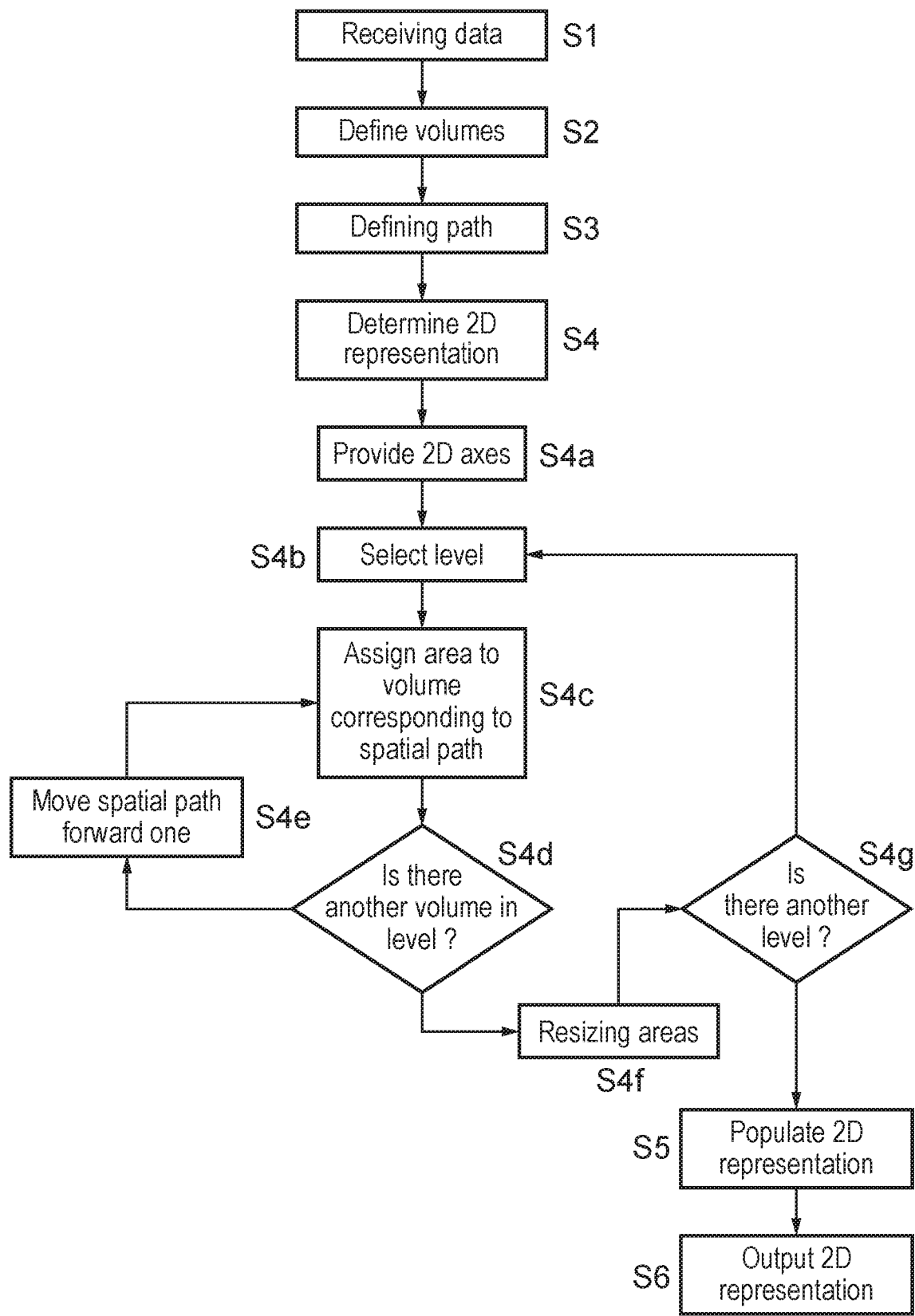
FIG. 5 is a flowchart showing an example computer-implemented method for generating a 2D representation as described herein.

Once the three-dimensional data is received, for example, from an imaging system, a computer, an image database, etc., the method of FIG. 5 proceeds to transform the three-dimensional data into a two-dimensional representation. The present approach makes use of the hierarchy between levels/regions of an organ and represents the physical measurement data at each of the hierarchical levels/regions.

A hierarchical structure of an organ can be established by anatomical and/or functional characteristics. Generally, a hierarchical structure comprises a number of levels each containing a number of elements. An element from a higher level is related to one or more of the elements on the directly descending level, thereby producing a tree-like or finger-like arrangement having a number of branches/fingers. For example, the brain can be separated into lobes, each of which has its own anatomical function. The frontal lobe, responsible for executive functions can itself be separated into specific sub-regions or elements with dedicated functional subtasks, such as the area of Broca related to the speech, the precentral gyrus that controls the voluntary movements, and the premotor area that deals with the programming of voluntary motor movements. A hierarchical structure is also used for other organs such as the liver. In this case, the functional regions are separated with respect to the vascular supply and these divisions, known as Couinaud classification, are used to establish resection boundaries during surgery.

Although not directly related to a known function, other hierarchical divisions of large areas of tissues can be used clinically, e.g. the octants of a stereotaxic atlas can be used to divide an organ into its left/right, anterior/posterior and superior/inferior parts. Additionally, other coordinate frames, such as the distance to a specific reference region (e.g. the ventricles), can be used to further separate an organ into anatomically or functionally relevant areas. For example, the ventricular distance is thought to be clinically relevant as it is assumed to reflect differences in etiology and in clinical symptoms; see the guidance of Kim et al. [3]. Thus many organs can be classified into hierarchical structures based on other characteristics or functions as appropriate.

Taking the brain as an example organ for which a hierarchical structure can be defined, the whole brain (or cortex) can be divided into left and right sides or lobes, thus defining a first (top) hierarchical level comprised of two elements (left lobe and right lobe). The left and right lobes can each be further divided into frontal, temporal, occipital and parietal lobes, cingulate cortex, and insula cortex. This defines a second hierarchical level, descending in hierarchy from (i.e. immediately below) the first level, and comprising a total of twelve elements (left frontal lobe, left temporal lobe, etc.). In this regard, it should be understood that the element (left lobe) of the first hierarchical level is directly related to/superordinate to (or parent of) the descending six elements (left frontal lobe, left temporal lobe, left occipital lobe . . . etc.). Such a hierarchical structure can continue, defining many levels and elements accordingly.

Figure 6:
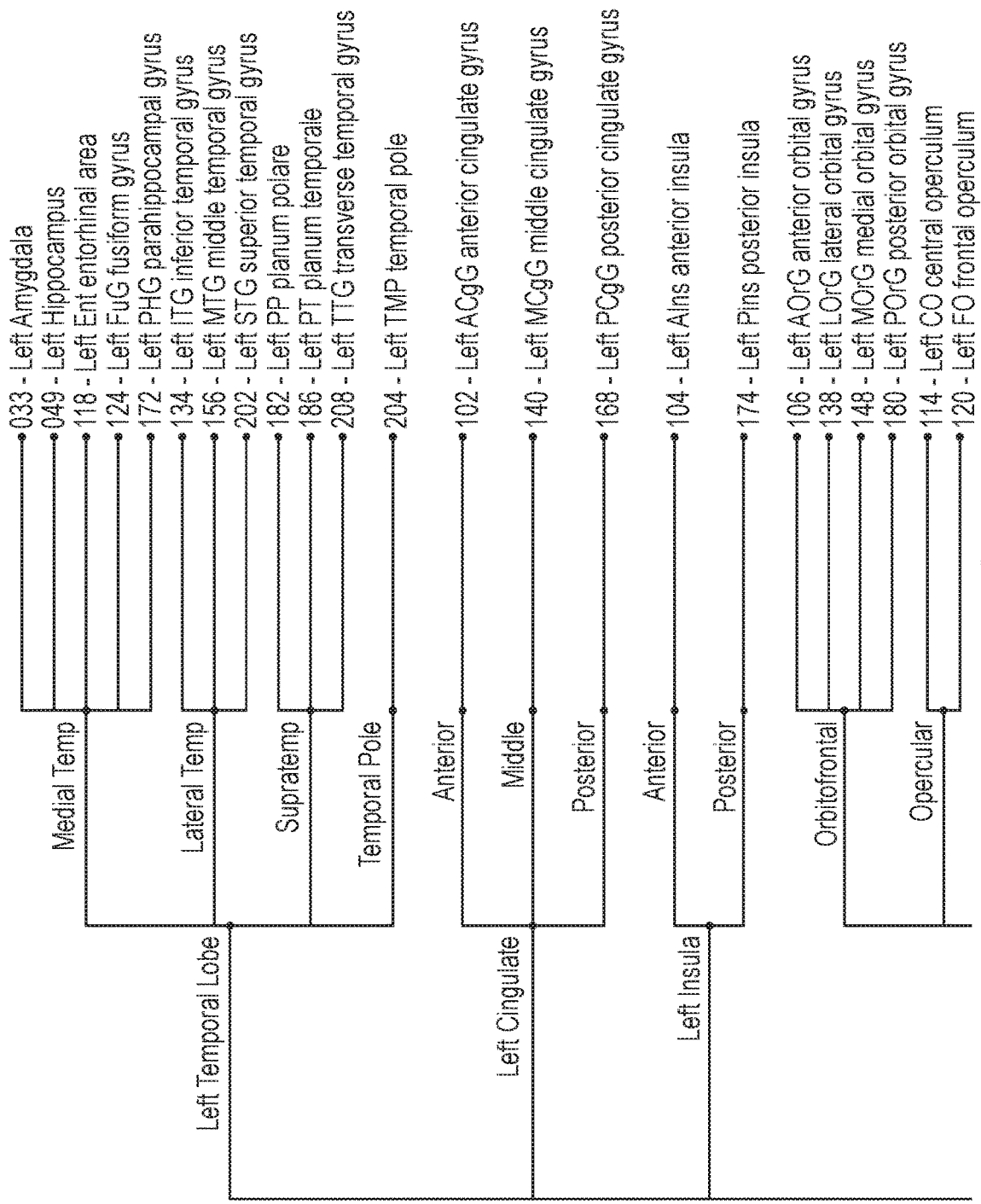
FIG. 6 represents an example hierarchical structure of regions/volumes of the brain starting from the left lobe/cortex of the brain.
Figure 6:
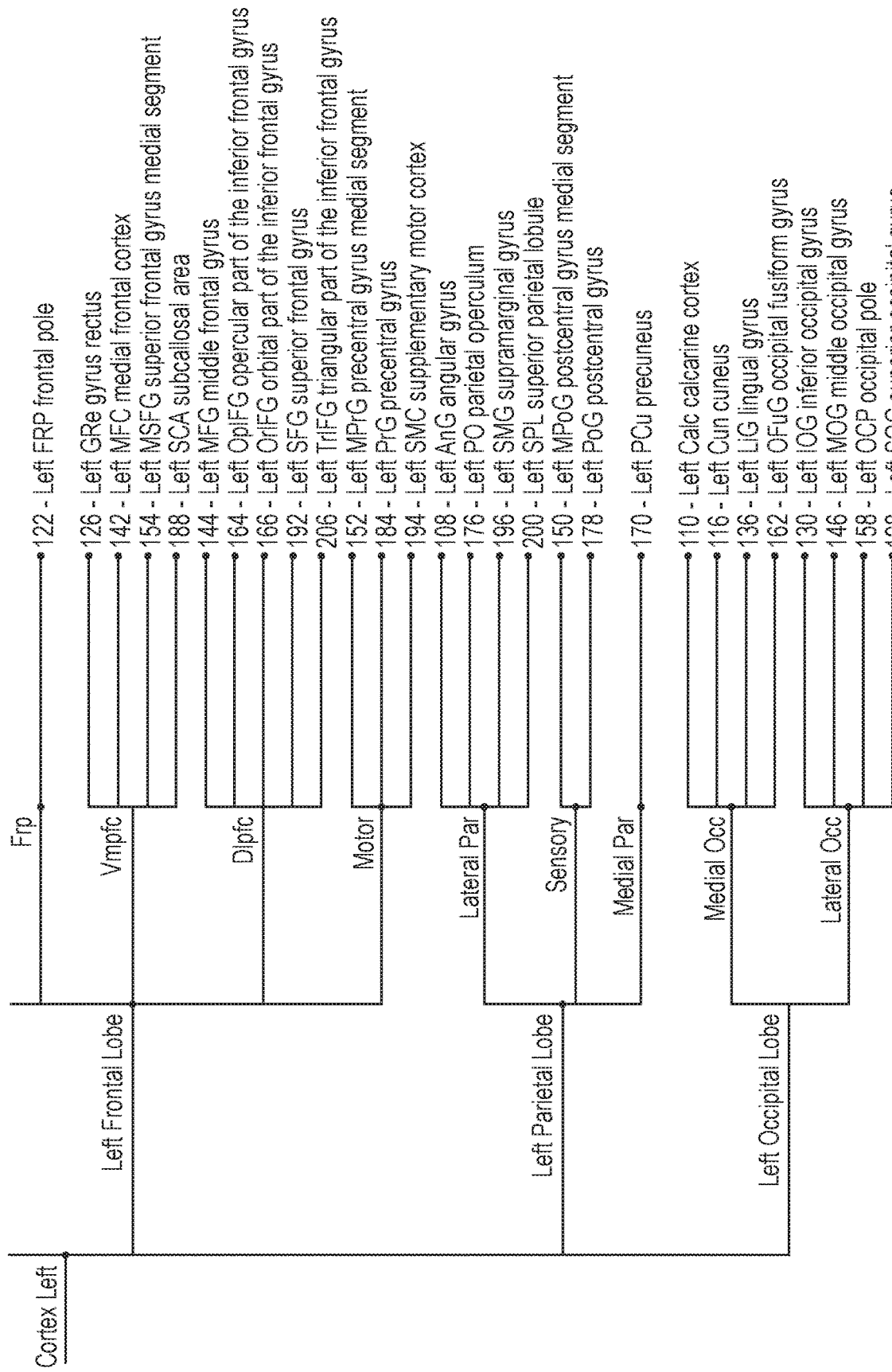

An example (albeit much more complex than defined above) of such a hierarchical structure is seen in FIG. 6. This Figure shows the relationships between various anatomical or functional regions of the brain, starting at the left cortex for reasons of presentation. That is, FIG. 6 shows the hierarchical structure of the left cortex/lobe. It should be understood that a similar or identical/symmetric hierarchical structure is possible for the right lobe. The top (root) of the hierarchy is shown to the far left, and contains a single element (cortex left), while the lower levels of the hierarchy (sometimes referred to as leaves) are shown to the far right. Therefore moving from left to right is equivalent to descending through the hierarchy. Each of the elements in a lower hierarchical level relates to (descends from) one element of the immediate higher hierarchical level. For example, the left temporal lobe is subordinate to (descends from) the left lobe. Thus FIG. 6 shows the relationships of elements of a given hierarchical level to elements of the hierarchical levels immediately above and below the given hierarchical level.

It should be understood that FIG. 6 shows one representation of the anatomical relationships between regions or volumes of the brain; the skilled person will appreciate that other structures may be developed or utilised, depending upon the particular properties under investigation. In addition, although the terms used in FIG. 6 to describe the regions are generally medically accepted, the hierarchical relationships may vary depending upon the choice of which elements are included in which hierarchical levels or which elements are correspondingly grouped together.

Returning to the method of FIG. 5, the transformation proceeds to use the hierarchical structure of the biological organ to define a series of volumes within the three-dimensional physical measurement data of the organ at step S2. In this regard, the method may include the step of calculating or determining, for each element of the hierarchical structure, a corresponding volume (region) in the three-dimensional space of the physical organ. Accordingly, all of the physical measurement data that falls within the volume determined for a given element is associated with that element.

This spatial division of the original 3-D data set into various biological components (different organs, and components of these organs) is referred to as a segmentation or parcellation. Various tools exist to perform this processing, which may also be performed by hand with respect to image data. The segmentation/parcellation of the original 3-D data set may be performed prior to the processing of FIG. 5 (i.e. so that the received data has already been segmented as appropriate), and can be accommodated as part of the overall processing of FIG. 5.

Each of the elements is processed in the same way so that each element is associated with a volume that corresponds to a subset of the three-dimensional physical measurement data. Note that as we move up the hierarchy, the volume for a given element may just represent the sum of all the volumes that descend from the given element (i.e. that are lower than the given element on that particular branch of the hierarchical tree). In addition, it should be understood that one measurement point may be associated with several volumes, depending upon how the hierarchical anatomical regions overlap. Another possibility is that volumes corresponding to each element may be processed or determined using the input data (e.g. the raw images). The volumes determined in this manner may then be transposed over into the three-dimensional measurement data. In both cases, volumes are defined within the biological organ corresponding to the elements of a hierarchical structure to which the physical measurement data is or can be associated.

A further possibility is that the volumes are defined according to a standard template that maps hierarchical relationships to a standard organ. Such a standard template may then be registered (rigidly or non-rigidly as appropriate) to the obtained images and/or physical measurement data. The use of such a standard template may reduce the processing time associated with defining volumes independently, since the registration of the template may only require matching a small number of registration points to obtain a reasonably accurate fit for each region. This is particularly the case for organs which generally do not experience a substantial change in the relative position and/or size of the elements of the hierarchical structure between patients or subjects.

After step S2 has divided the organ into a number of volumes or elements of the hierarchical structure, step S3 defines one or more spatial paths through the three dimensional volume of the organ. Thus in the two-dimensional representation output by the method of FIG. 5, a first axis is defined by hierarchical level, as determined in step S2, while a second axis is defined by position along the spatial path, as determined in step S3. A given volume or element can then be located within the two-dimensional representation once the level of the element, and its position along the spatial path (for that level), are known.

Overall, the spatial path seeks to represent the spatial arrangement of elements within a given hierarchical level. For example, the spatial path may begin at the volume of the organ corresponding to a first element of a hierarchical level. The spatial path then proceeds to pass through the volume corresponding to a second element of the same hierarchical level physically adjacent or proximate the volume of the first element. The spatial path continues to pass through volumes in this way through all the elements of the hierarchical level. Although the single axis of the spatial path cannot fully capture the spatial arrangement (relative locations) of the elements in three-dimensional space, nevertheless, the ordering along the spatial path can help a practitioner intuitively understand and recognise the spatial relationships between the different displayed elements, especially when the spatial path preserves symmetry (as discussed in more detail below).

The spatial path therefore comprises a hypothetical line or trace through the biological organ in three-dimensional space that sequentially passes through volumes or regions of the biological organ corresponding to the elements of a given hierarchical level. In particular, the spatial path defines a sequence or ordering of the elements at a given hierarchical level (so that there may be multiple spatial paths, one for each hierarchical level)—i.e. the ordering of the elements along the second axis corresponds to the order in which the elements are encountered along the spatial path. The spatial path is generally selected or determined such that each element at a given hierarchical level only appears once along the spatial path (and hence once in the representation). If two elements are adjacent to one another along the spatial path, this generally implies that they are adjacent to one another in three-dimensional space.

Some elements within the biological organ might be excluded from the spatial path, e.g. if such elements are not pathologically relevant, and hence would be of little or no interest for a practitioner. In this case such an exclusion might be implemented (for example) by: (i) routing the spatial path around the element; (ii) including a jump or discontinuity in the spatial path to avoid the element; or (iii) having the spatial path go through the element, but ignoring the element in the ordering of the second axis. Note that the same options might also be employed to avoid a given element appearing more than once along the spatial path.

The spatial path (at each hierarchical level) is therefore meant to reflect, as far as possible, the relative spatial (physical) positioning of the various elements, having potential regard also for any relevant the biological factors. For example, a spatial path in the brain may extend in a straight line from the left (or right) lobe to the right (or left) lobe to define a spatial path through the three-dimensional volume of the organ at the highest (first) hierarchical level. A more complex spatial path can be defined for the next level, whereby the spatial path may start at the left parietal lobe, move next to the left occipital lobe, then the left temporal lobe, then the left frontal lobe, onto the right frontal lobe, to the right temporal lobe, etc. In other words, the spatial path spatially connects the volumes of a given hierarchical level and, in effect, determines a sequence of volumes within that given hierarchical level.

As an example of a spatial path, in a given hierarchical level, there might be 4 regions or elements having an approximately planar configuration as shown in the table below:

TABLE 1

| A1 | B1 |
|----|----|
| D1 | C1 |

The spatial path might then be defined so as to pass through (in order) A1-B1-C1-D1. With this ordering, it can be seen that two elements which are adjacent to one another in the spatial path always have a common face, and therefore can be considered as next to one other in the original spatial arrangement. Furthermore, as discussed in more detail below, such an ordering can preserve both left-right symmetry (A1-B1 and D1-C1), as well as front-back symmetry (A1-D1 and B1-C1), A more complex 3-D distribution of elements might be formed as follows:

TABLE 2

| A1 | B1 |
|----|----|
| D1 | C1 |
| A2 | B2 |
| D2 | C2 |

In this configuration, it is assumed that each of the 8 elements represents a corner of a cube, with element A1 located above element A2, element B1 located above element B2, and so on. One potential spatial path through these regions might be defined as A1-B1-C1-D1-D2-C2-B2-A2. Again with this ordering, it can be seen that two elements which are adjacent to one another in the spatial path always have a common face, and therefore can be considered as next to one other in the original (3-D) spatial arrangement. As discussed in more detail below, such a path could preserve front/back symmetry, and also top-bottom symmetry, but not left-right symmetry. However, if it was more important to preserve left-right symmetry and front-back symmetry (for example), a different spatial path might be chosen, such as: A1-A2-D2-D1-C1-C2-B2-B1.

It will be seen therefore that there may be multiple possible spatial paths through a given organ. The determination of which particular spatial path to utilise may be based on a number of factors, including which axes of symmetry to preserve (if any), as discussed above, and also biological relevance. For example, a given element may have multiple neighbouring elements. There may be significant biological interaction between the given element and a first one of these neighbours, but far less biological interaction between the given element and the other neighbours. In this situation, it would generally be desirable for the given element to be adjacent to the first neighbour along the spatial path. In other words, the spatial path (and hence the ordering along the second axis) would then reflect not only the original 3-D spatial relationships between elements, but also biological relationships or interactions.

Each hierarchical level may be provided with a spatial path. The ordering of the spatial path will also usually group sibling elements together based on the hierarchical structure (siblings being those elements that are immediately descended from a given element in the immediately higher level, in other words, those elements that all have a common parent). The ordering of the spatial path then also defines a sequence or ordering within each group of sibling elements. The spatial path of a lower level may be determined, at least in part, based on the spatial path defined in the immediately higher level. That is, for example, the spatial path of the first hierarchical level constrains the freedom in defining the spatial path of the second hierarchical level in order to respect the sibling relationships mentioned above.

It may also be possible to define only a single spatial path which passes through the lowermost elements of each branch of the hierarchical structure. If the sibling relationships are respected by the path (that is, siblings in a level are grouped together), then this single spatial path can also be used to define the spatial path at all higher levels of the hierarchy. For example, assume the second hierarchical level can be considered to comprise the lowest element for each branch. A spatial path that moves through the volumes of the second hierarchical level also moves through the first hierarchical level (e.g. left lobe to right lobe) and so can be used for both hierarchical levels.

For example, in the case of a hierarchical structure for the brain, the spatial path of the first hierarchical level may move from the left lobe to the right lobe, and the spatial path for the second hierarchical level is then defined such that it passes through elements associated with (located in) the left lobe before passing to the right lobe. (In this case, the elements of the left lobe are siblings, because they share a common parent element, namely the left lobe, likewise for the elements of the right lobe). Extending this to the third level, a spatial path might start at the left lateral parietal lobe (of the left parietal lobe), for example.

Overall, one or more spatial paths are therefore defined based upon moving through the volume of the organ related to the elements of the hierarchical structure. It should be appreciated that the spatial paths are defined such that they pass sequentially through volumes in order to preserve some spatial ordering. In addition, the spatial paths are not limited as regards the direction in which they propagate through the three-dimensional volume. That is, the spatial path may move in an x, y, or z-direction from one volume to the next, or indeed in any combination of directions. (The spatial path may also jump, e.g. to avoid a volume or element that has already been included earlier along the spatial path, or to avoid a volume or element which is of little or no clinical interest for a given investigation). Thus the spatial path may pass through all elements of a given hierarchical level (or through all elements in the organ) or alternatively, the spatial path may not pass through all the elements of a given hierarchical level. For example, the exemplary spatial path for the second hierarchical level given above may not pass through the left occipital lobe. Reasons for omitting certain regions/volumes/elements from the spatial path may be due to the fact that the volumes of the organ corresponding to these elements may not have any impact in the pathological condition underlying the medical assessment to be performed and thus do not need to be presented to the medical practitioner. The spatial path still preserves relative spatial positions of the selected elements (or corresponding volumes in the organ) to one another but in effect bypasses elements that are not desired to be displayed.

In practice, one or more standard spatial paths may be predefined for a given organ. In this case, step S3 may comprise selecting one of these standard, predefined paths. In some cases, a user might modify such a standard, predefined path to reflect better the present circumstances (or might define their own, new spatial path).

Once the spatial path(s) have been defined, the method proceeds to step S4, in which the 3D physical measurements are transformed into a two-dimensional representation. In one implementation, step S4 is broken down into sub-steps as described herein. Step S4$a$ involves defining the two-dimensional axes for the two-dimensional representation, wherein the first axis corresponds to the spatial path through the three-dimensional volumes, while the second axis corresponds to descending successive levels through the hierarchical structure.

Figure 7:
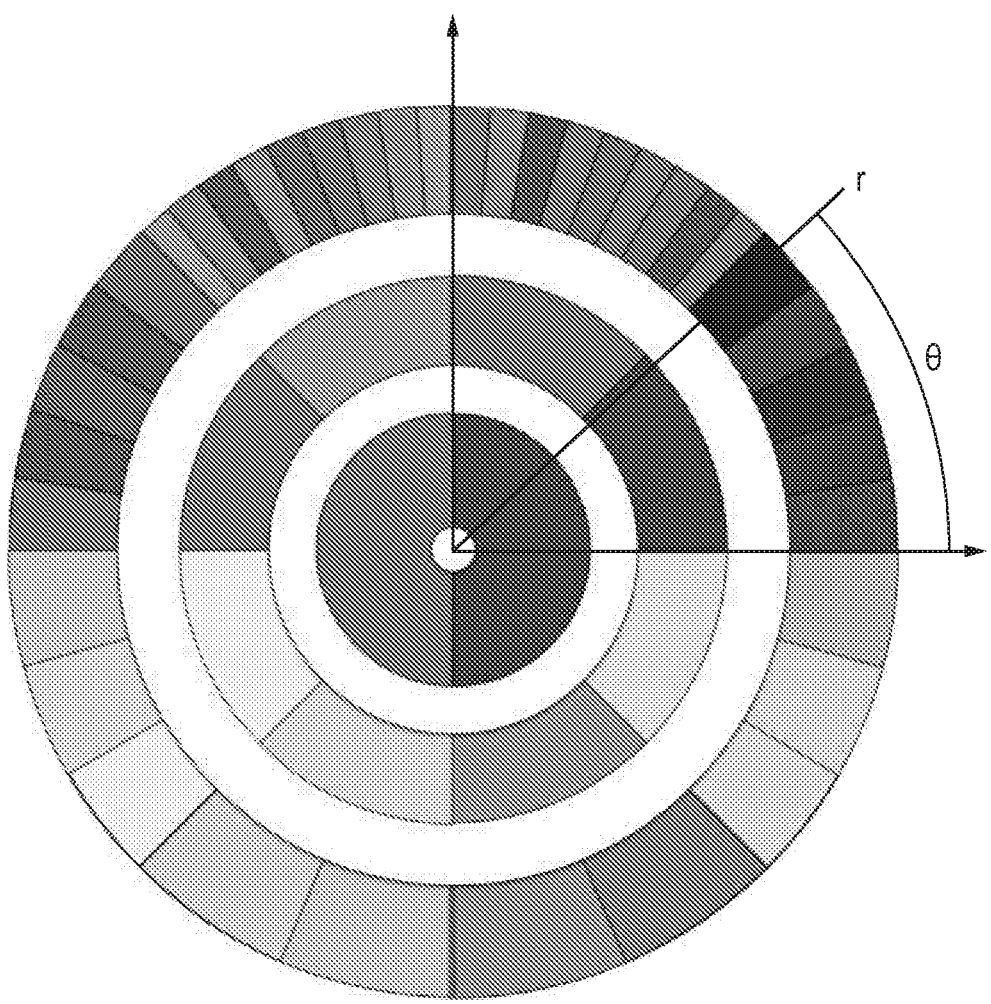
FIG. 7 illustrates a two-dimensional representation as generated herein using concentric rings indicative of a hierarchical relationship.

With reference to FIG. 7, an example of a two-dimensional representation is defined in a polar coordinate frame and, as such, has two axes corresponding to radial position r and angular position $\theta$. In this implementation, the angular coordinate corresponds to the spatial path through the three-dimensional volume (first axis), while the radial coordinate corresponds to the descent through successive hierarchical levels (second axis).

Once the two-dimensional axes have been established (and clearly this may be determined for a particular type of data set), the method proceeds to determine the areas within the two-dimensional representation. The areas may be determined according to a variety of methods, several of which are discussed below, but most typically they correspond to volumes or elements of the hierarchical structure.

The method now proceeds to step S4$b$ and selects a hierarchical level to populate. In effect, this step involves selecting a coordinate of the second axis which represents depth in the hierarchy (the radial coordinate in FIG. 7) and keeping this fixed for the duration of the processing loop for a given hierarchical level.

In step S4$c$, we now in effect follow the spatial path through the selected hierarchical level, processing each element in turn in the order encountered along the spatial path. As part of this processing, we assign an area in the 2D representation to the element (and hence corresponding volume) indicated by the current position of the spatial path. The ordering of the areas for the volumes along the first axis (for the fixed coordinate in the second axis) corresponds to (matches) the ordering of the volumes along the spatial path. The size of the allocated areas may reflect, at least in part, the size of the corresponding volumes.

After allocating an area for a given volume, step S4$d$ determines whether or not there is another volume within the hierarchical level selected at step S4$b$. If yes, at step S4$d$, the method proceeds to step S4$e$, in which we advance one volume or region along the spatial path; we then return to Step 4$c$ to determine the area ($\theta$ coordinates) to represent this next element. It will be appreciated that this newly determined area will be directly adjacent to the area of the immediately preceding element. At some point, at step S4$d$ the determination is in the negative (because all volumes in the relevant hierarchical level are accounted for) and so the method proceeds to step S4$g$.

In some implementations, step S4$d$ may include a "skip" option. In this case, a user (or a computer automatically in accordance with predefined criteria which might be specific for a certain pathological condition) may choose to skip the next volume in the spatial path if, for example, the next volume is not considered to be pathologically relevant. So, for example, before progressing to step S4$f$ or S4$g$, step S4$d$ may ask not only if a next volume is present but also whether that next element is to be processed for the transformation (whether it is pathologically relevant). In this way, the produced two-dimensional representation may select information that is relevant to the medical practitioner while skipping information that is not.

FIG. 5 also shows an optional step S4$f$, performed after a given level has been fully incorporated into the two-dimensional representation (when it is known how many elements are to be accommodated in this level). For example, optional step S4$f$ may adjust the size of the areas in the two-dimensional representation such the sizes of the areas are all equal. For the example of FIG. 7, at the first level of the hierarchy, this may involve providing two areas that span 180° each. Other ways of resizing are possible, or in other implementations step 4f may be omitted altogether. For example, the elements and hence corresponding volumes of any given hierarchical level are known at the time of step S4c, and hence an appropriate area sizing (having regard to all the elements in this hierarchical level) may be determined as part of step S4c itself.

After the completion of step S4f (if utilised) we proceed to step S4g, which determines whether or not there is another hierarchical level in the hierarchical structure that is yet to be assigned areas in the two-dimensional representation. If the answer is no, the method proceeds to step S5. If, however, the answer is yes, then the method returns to step S4b, and the above procedure is repeated for the next hierarchical level. As discussed above, the radial coordinate corresponds to hierarchical level, so when the method loops back to step S4b, the radial coordinate is typically changed to the next level down in the hierarchy. Thereafter, the method proceeds through the steps as described above, in effect looping or iterating until all hierarchical levels have been processed.

At step S5, the physical measurement data is populated in the two-dimensional representation. Each area within the two-dimensional representation corresponds to a volume including the three-dimensional physical measurement data by virtue of steps S4a-S4g described above. Therefore, in this step, an indication or representation of the physical measurement data is provided/assigned to the area corresponding to this volume. Several options for implementing this are discussed below. As one example, the physical measurement data may be denoted by colour, wherein the colour is indicative of the (average) value of the physical measurement data within the volume. In particular, there can be a scale which maps data value to colour, such that each area of the representation may be assigned a corresponding colour based on the measurement data within the volume represented by the area.

At step S6, the generated two-dimensional representation may be output to a display apparatus, e.g. a laptop or tablet computer, for display to, e.g., a medical practitioner. The display apparatus may have a processor or renderer capable of drawing or rending the two-dimensional representation on the display.

Figure 8:
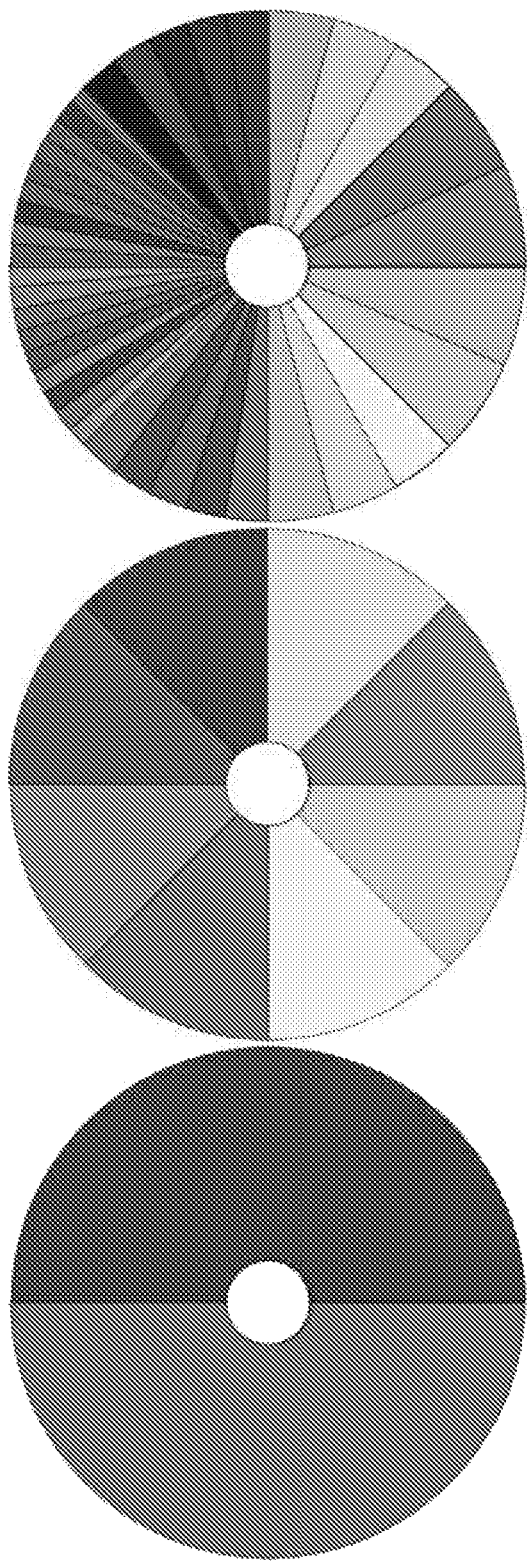
FIG. 8 illustrates represents each of the concentric rings of FIG. 7 in an exploded view.

FIG. 7 exemplifies the displayed output of the two-dimensional representation. In FIG. 7, three concentric rings are shown, each ring corresponding to a different, respective hierarchical level. As described, the radial coordinate indicates level in the anatomically defined hierarchy, while the angular coordinate corresponds to the spatial path through a given hierarchical level. FIG. 8 shows the same three rings, but in an expanded view, in which each ring is presented separately (rather than concentrically), side-by-side, such that moving from left to right corresponds to descending the hierarchy. Note that the colours shown in FIGS. 7 and 8 are just used to represent the different regions/elements of the hierarchical structure only, and are not indicative of the values of any physical measurement data.

Figure 4:
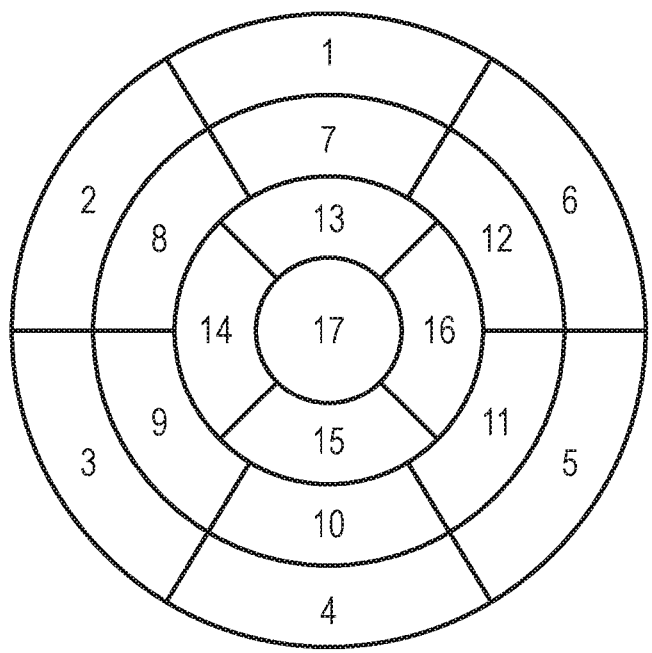
FIG. 4 shows a known scheme for left ventricular segmentation.
Figure 9:
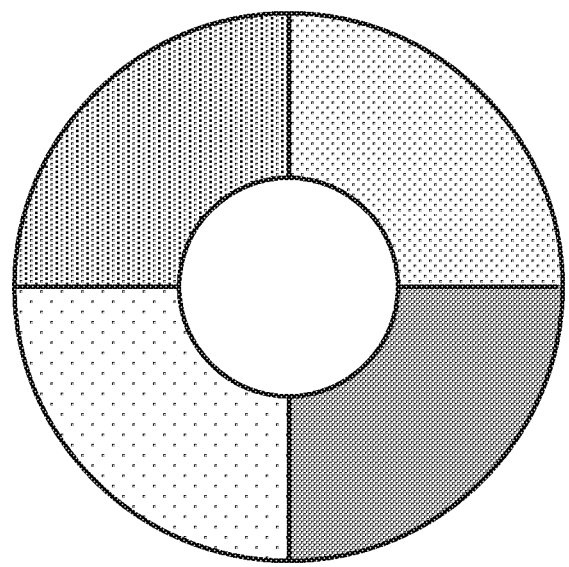
FIG. 9 represents an example mapping of brain regions/volumes to regions of a two-dimensional representation.
Figure 9:
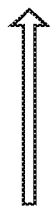
Figure 9:
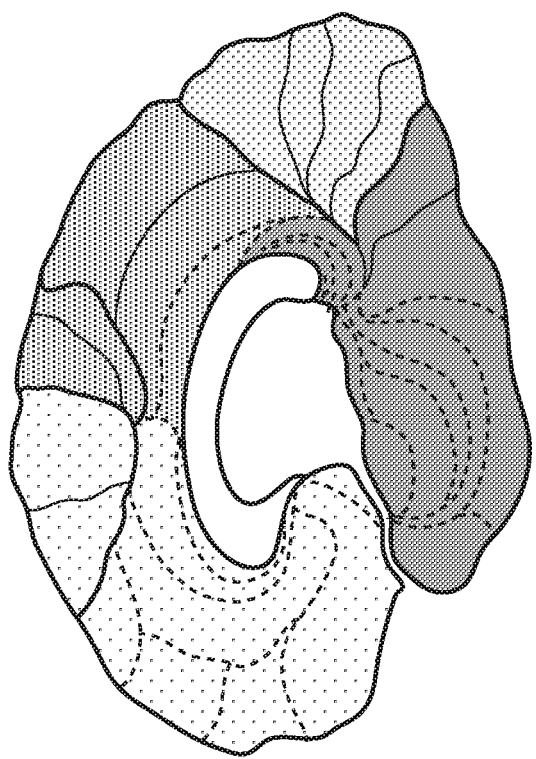

FIG. 9 shows an example of the transformation of FIG. 4 applied to the lobar regions to generate a ring. In other words, this Figure shows how the volumes of a top hierarchical level have been assigned areas in a two-dimensional representation (concentric ring). In this case, the spatial path is defined to move in a clockwise direction starting in the region shown in yellow, and then moving in sequence through the green region, the blue region, and ending in the pink region. Note that since the representation of FIG. 9 is circular, the spatial path can likewise be considered as a closed loop. Accordingly, it is somewhat arbitrary which coloured region is regarded as the first element along the spatial path, and also in which quadrant this first element is then depicted (and whether the ordering of the spatial path is shown in clockwise or anti-clockwise fashion).

This above-described method illustrates an example process for projecting a predefined set of hierarchical data obtained from imaging-derived measurements into a two-dimensional (planar) graphical representation in an anatomically informative manner. Such a tool is specifically designed with regard to the 3D nature of human organs having a hierarchical structure of anatomical or functional regions. The three-dimensional to two-dimensional transformation respects the anatomical relationship between the regions of the organ, rather than using a more mathematical or geometrical projection or constructs such as conformal mapping. This approach helps to preserve important biological relationships in the measurement data, which can provide important cues for medical diagnosis, such as the expected left-right anatomical symmetry in the healthy human brain. Other symmetries, such as superior/inferior and medial/lateral (or distal) symmetry, of the organ can also be preserved by appropriate configuration of the 2D representation (e.g. by selection of a suitable spatial path).

While different hierarchical levels and the corresponding anatomical elements are encoded using the two-dimensional coordinates, the physical measurement data can be encoded, for example, using a colour scale. In this approach, the physical measurement data within the original 3-D volume are allocated to the different elements of the organ—this may involve using a segmentation algorithm. The physical measurement data for a particular element are then averaged or otherwise process within the element (if required) to give a value (or values) which can then be mapped to a given colour using a colour scale. One known form of colour scale is based on colours for increasing temperature, in which the peak wavelength decreases with increasing temperature—e.g. red, then orange, then yellow, and so on through the colour of the rainbow. Elements having higher values for the physical measurement data are mapped to colours representing higher temperature, and can then be displayed accordingly. This type of representation is often referred to as a heat map, and can help a medical practitioner grasp from one representation the overall distribution of the physical measurements (e.g. biomarker concentration) through the biological order, and this in turn may help to improve diagnosis, clinical decision-making, and improving clinical confidence, and so on.

One skilled in the art will appreciate that although the processing of the physical measurement data is described as separate from the steps shown in FIG. 5, this is not necessarily the case. Overall, the processing may be performed in any reasonable order, as appropriate to the particular circumstances of any given implementation, including the exact nature of the hierarchical structure used, the biological organ of interest, etc. For example, the physical measurement data might be mapped a colour (according to the colour scale) while still in three-dimensional form. This colour would then be carried through from the 3D volume elements into the corresponding elements in the 2D representation.

As mentioned above, the areas or regions of the two-dimensional representation corresponding to each element can be determined (at step S4f) in a number of ways. For example, the elements in the same hierarchical level may all be given the same size. This approach is employed in the representation of FIG. 7 for the inside and middle rings. The outer ring of FIG. 7 adopts a somewhat different approach, in the each group of siblings within the outer ring is given the same area. In addition, the siblings within any given group are likewise all given the same area. However, since the number of siblings may vary from one group to another, the area allocated to an element (sibling) in one group may differ from the area allocated to an element (sibling) in a different group.

In other words, in this latter approach, the areas of the third hierarchical level (the outermost ring) are dependent upon the size of the area assigned to the corresponding (parent) element in the second hierarchical level (i.e. the immediately higher level). In this regard, the total area available is defined by the angle defined by the edge of the area of the parent element in the second hierarchical level. This approach ensures that a single branch fits within a corresponding sector of the ring.

As an example, the yellow segment in the middle ring, which is located between the angles of 225 and 270 degrees (clockwise) with respect to the central upright ("12 o'clock") position, corresponds or branches out to three separate subordinate (child) elements in the outer ring, each of which is indicated by its own shade of yellow. Each yellow element in the outer ring therefore subtends an angle ($\theta$) of 15 degrees (since 45/3=15). In contrast, the red segment in the middle ring, which is located between the angles of 270 and 315 degrees (clockwise) with respect to the central upright ("12 o'clock") position, corresponds or branches out to five separate subordinate (child) elements in the outer ring, each of which is indicated by its own shade of red. Each red element in the outer ring therefore subtends an angle ($\theta$) of 9 degrees (since 45/5=9).

In another example, the size of the area assigned to an element in the two-dimensional representation is dependent upon the relative physical size (volume) of the element in the original 3D physical space. For example, the total volume of elements within a given hierarchical level may be calculated, and for each element in the hierarchical level, the percentage that it contributes to the total volume of the hierarchical level is determined. These percentage figures can then be used to determine the relative sizing of each area assigned to the elements in a given hierarchical level. Alternatively, the relative sizing is with respect to the total volume available to a group of siblings (as above), rather than with respect to the total volume available to the hierarchical level as a whole.

This latter approach has a couple of advantages. Firstly, because the sizing of the elements in the plot corresponds to their physical size in 3-dimensional space, it may be easier for a user to quickly appreciate which area in the representation corresponds to which hierarchical region in the 3D space. Secondly, the relative sizing of the different areas may also help to underscore the significance of the physical measurement data. For example, a given area may be colour-coded as described above to indicate a high concentration of a particular biomarker. If this area is also allocated a relatively large sizing (because the corresponding element has a relatively large volume), then it is readily apparent from the representation that a large amount of the biomarker is present (a high concentration across a large area/volume).

In another example, the size of the area assigned to an element in the two-dimensional representation is dependent upon the number of subordinate (sibling) elements directly descendent from the element. For example, an element in a given hierarchal level may have several elements that descend from the element in a higher hierarchical level. To ensure that all the sibling elements are displayed correctly and are visible to a medical practitioner, the superordinate element may be sized relative to the number of sibling elements. The sizing may also require that the elements of a given hierarchical level subtend a minimum angle (e.g., 2 degrees) or are a minimum width (both of which may vary for each hierarchical level).

In a further example, the size of the area assigned to an element in the two-dimensional representation is dependent upon a weighting assigned to the element. For example, in a given hierarchical level, each element may be assigned a weighting, wherein the total sum of the weightings of all elements equals one (or 100%). In this way, the elements are sized within the given hierarchical level based on the weightings. These weightings may be assigned automatically based on a pre-defined template/standard, or may be assigned by a user. The weightings may indicate, for example, the pathological significance of each element (volume) of the organ for certain conditions. For example, certain elements may be more pathologically relevant for studying epilepsy and thus it may be advantageous to display these elements more prominently in a 2D representation to the medical practitioner. It will be appreciated that the above examples of calculating the areas for elements in the two-dimensional representations are provided as examples only, and methods for calculating the areas can be employed as appropriate. Moreover, any combination of the methods may be used, and the method used may also vary within an individual plot across the different hierarchical levels (concentric rings)—as indeed is the case for FIG. 7.

In some cases, the hierarchical structure may be defined in such a way that not every branch has an equal depth. For example, some branches of the hierarchy may descend two levels, while other branches may descend only one level. In the context of FIG. 7, this might be represented by an incomplete ring—i.e. a portion of a ring is omitted at a position (angle) in the ring that corresponds to a branch that does not descend to this hierarchical level.

The transformation of FIG. 5 can be considered as a mapping of the original 3D data set into a specific 2D data representation based on the hierarchical structure for the organ, with one axis defined by hierarchical level, and the other axis defined by a spatial path through the elements in a given hierarchical. It will be appreciated that a 2D data representation is much easier to display, given that most display technologies, from printed paper through to computer screens, etc., are intrinsically two-dimensional in nature. Accordingly, such a 2D data representation is inherently compatible with a very wide range of display technologies. Furthermore, such a 2D representation is also compatible with the primarily surface-based paradigm of human visual perception—in other words, such a 2D representation may be easier and quicker to understand by a practitioner.

Note that the 2D data set resulting from the transformation of FIG. 5 can be displayed on a screen according to a number of strategies or formats. FIG. 7 as discussed above provides one such display strategy, which involves splitting a circular representation into concentric rings to represent the different levels of the hierarchy—although FIG. 7 does not illustrate any specific physical measurements of the organ.

Figure 10:
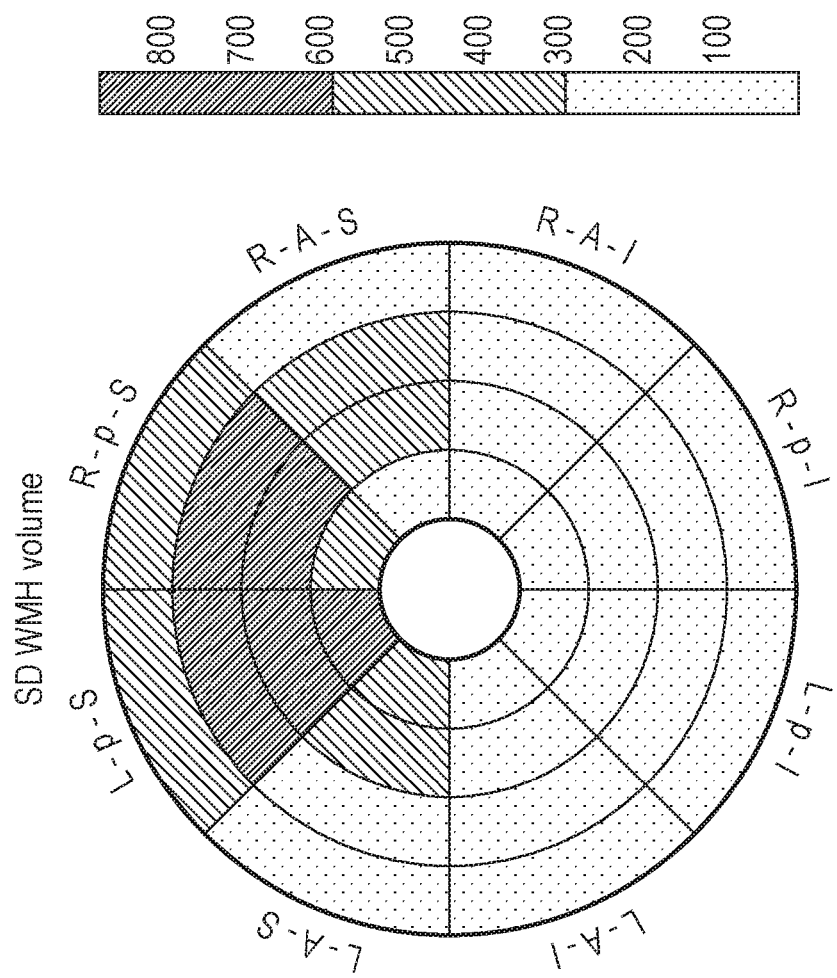
FIG. 10 illustrates raw grey matter measurements of a brain and a two-dimensional representation as described herein of the same data showing hierarchical relationships.
Figure 10:
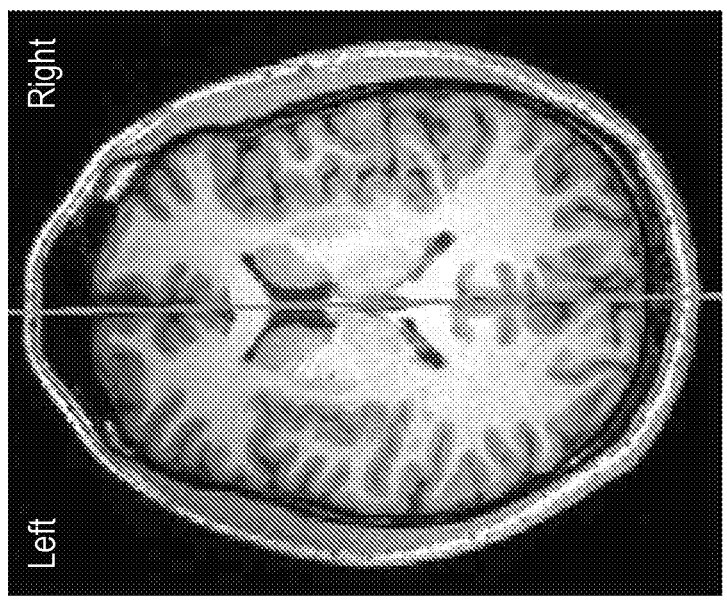

FIG. 10 shows an image and a plot derived from measurements of symmetrical white matter hyperintensity burden. In particular, the left-hand portion of FIG. 10 is an image or view obtained from a slice through the original 3D imaging (or measurements). Superimposed on this image is a line representing the division between the left and right regions of the brain. The right-hand portion of the brain is a 2D representation of the 3D measurements, complete with a colour scale to the right (this particular scale is not based on temperature colour). The general format of this latter plot is analogous to that of FIG. 7.

In addition, the 2D representation to the right of FIG. 10 generally preserves left-right symmetry from the original data set. This is achieved by having the spatial path used for ordering the regions in the left-hand half of the plot correspond to the spatial path used for ordering the regions in the right-hand half of the plot. In particular, the spatial path in the right-hand half is a mirror image (or approximately so), about the dividing line shown between the left and right regions, of the spatial path in the left-hand half of the image, so that the order of elements in the 2D representation is the same for both left and right hemispheres. This then allows the plot to convey and represent the degree of left-right asymmetry in the physical measurements, which is a useful clinical indicator for certain regions. The plot of FIG. 10 further provides an indication of higher levels of hyperintensity in certain regions, as indicated by the red colouring.

Figure 11:
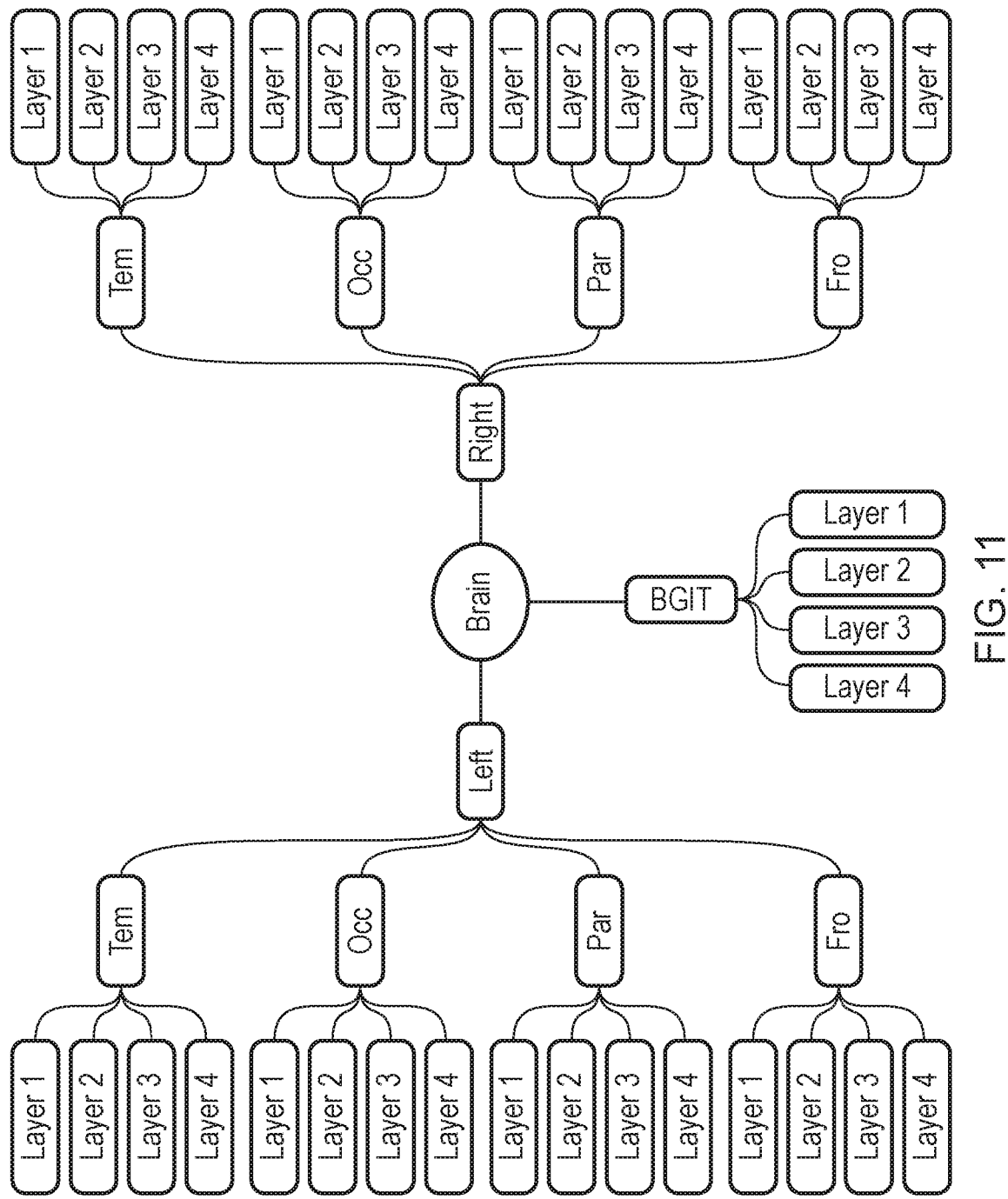
FIG. 11 shows an example hierarchical structure of the brain and a corresponding two-dimensional representation as described herein, indicating in particular lesion frequency in each of the (sub)volumes of the brain corresponding to the hierarchical elements.
Figure 11:
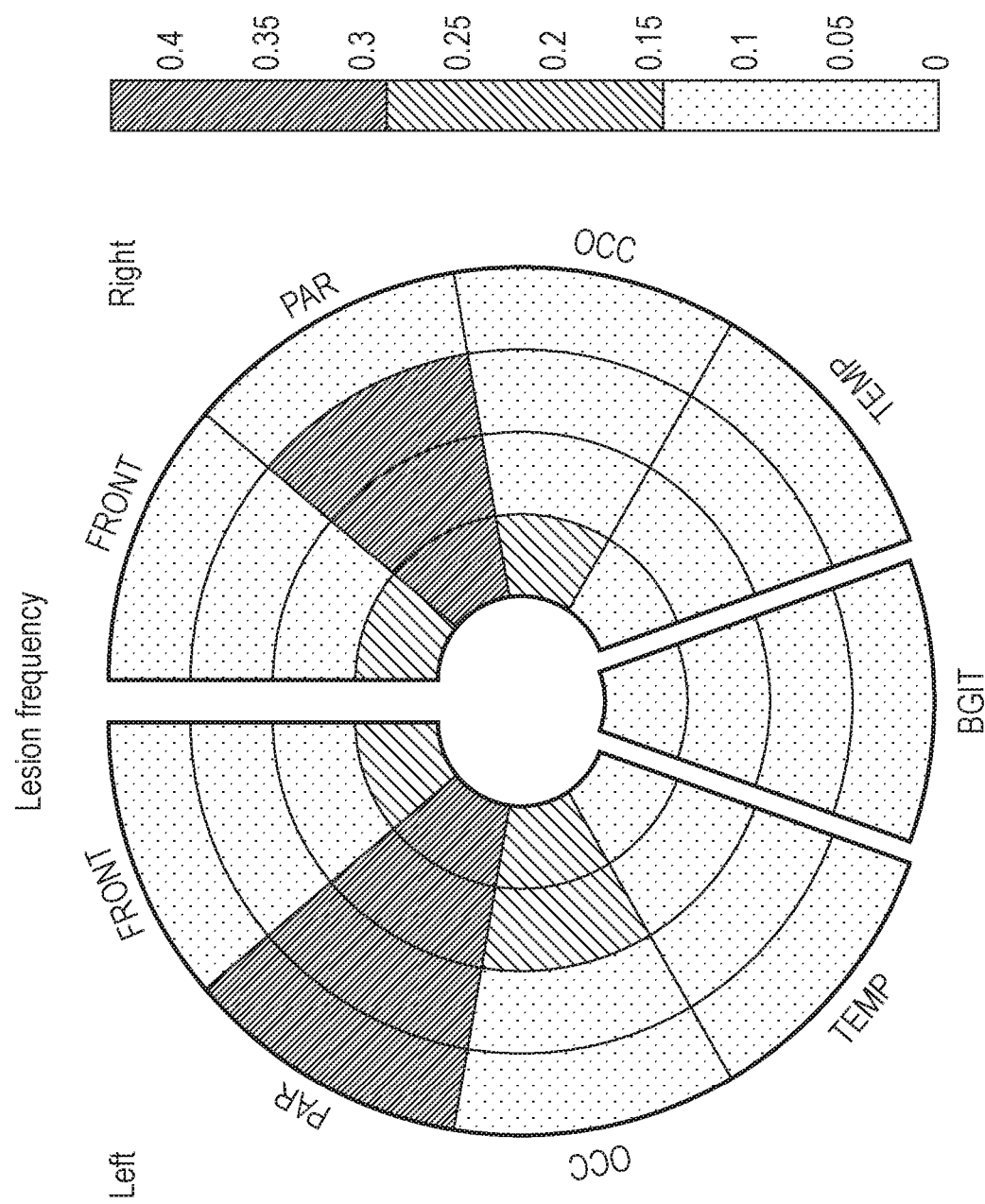

FIG. 11, left hand portion, presents a hypothetical anatomical hierarchy based on the parcellation of the cortical grey matter. The right-hand portion of FIG. 11 shows a two dimensional representation that follows this hierarchy, using substantially the same configuration of axes as for FIGS. 7 and 10, in which the radial axis corresponds to descent through the hierarchy, and angular or azimuthal position corresponds to a spatial path through regions at a particular hierarchical level. This layered spatial representation can subdivide, for example, different large white matter regions, such as axis-based or lobar-based, into their composing layers. The physical measurements represented in FIG. 11 indicate lesion frequency.

With reference to Tables 1 and 2 above, we note that an ordering of A1-B1-C1-D1 was defined for Table 1. If we assume that these elements are located clockwise around a circular plot such as shown in FIGS. 10 and 11, with A1 in the front left quadrant, B1 in the front right quadrant, etc, then the spatial path fully reflects the relative spatial locations of the four elements. In this case left-right symmetry is preserved (about the vertical axis of the plot) and front-back symmetry is also preserved (about the horizontal axis of the plot).

For Table 2, and the ordering A1-A2-D2-D1-C1-C2-B2-B1, and again adopting a clockwise representation of the elements for a plot such as shown in FIG. 10 or 11, this can lead to the arrangement shown below. This ordering preserves left-right symmetry (about the vertical axis) and also front-back symmetry (about the horizontal axis), however, top-bottom symmetry is lost (in the sense that it is not preserved as a reflective symmetry in the plot). The skilled person will therefore be able to maintain the symmetry axis (or axes) that are of most biological significance (for any given investigation).

|  | D1 | E1 |  |
|---|---|---|---|
| D2 |  |  | E2 |
| A2 |  |  | B2 |
|  | A1 | B1 |  |

Figure 12A:
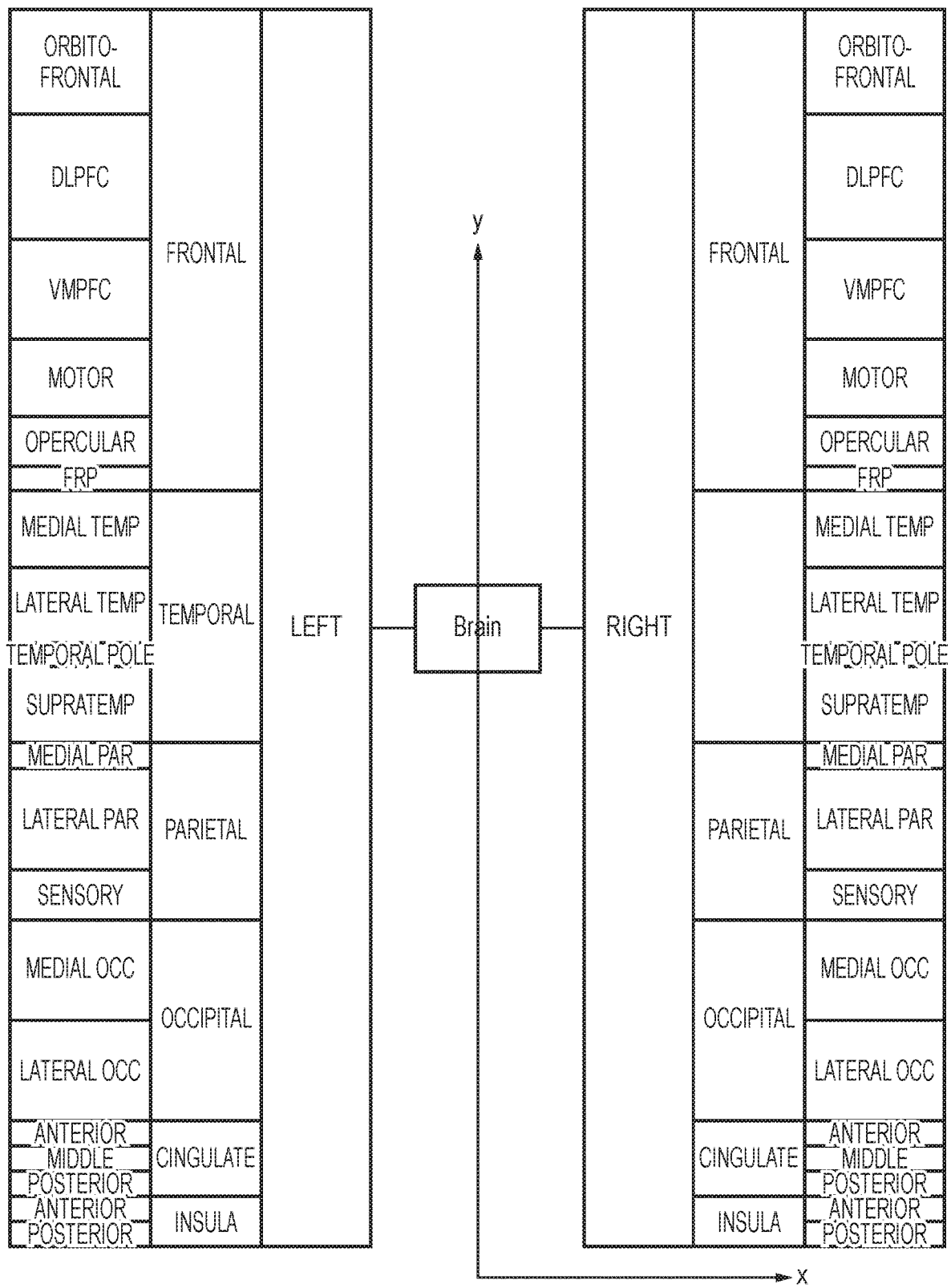
FIG. 12a schematically illustrates a Cartesian two-dimensional representation as described herein (as an alternative to the concentric rings of FIG. 7).

Although FIGS. 10 and 11 both use a circle-based plot for depicting the 2-D representation or data set obtained from the original 3-D volume, complete with a colour scale to indicate the physical measurement value for each of the plotted regions or locations, a variety of other presentations may be derived from a 2D data set structured in this manner. For example, FIG. 12a shows a linear (or Cartesian) representation, with the brain again being the chosen organ, which is divided into hierarchical regions. In the plot of FIG. 12a, the horizontal (X) axis is used to represent depth in the hierarchy, while the vertical (Y) axis is used to represent a spatial path through the regions at any given hierarchical level. The particular plot of FIG. 12a further shows the vertical direction split into two components, one corresponding to the left hemisphere, the other to the right hemisphere, which are then presented in an inverted or mirror relationship to one another. It will be appreciated that this configuration in effect preserves the original symmetry between the left and right hemispheres (as was also done for the plot of FIG. 10). Note that the colouring of FIG. 12a is only used to distinguish different brain regions, not to indicate the values of physical measurement data (such values are not indicated in FIG. 12a).

Figure 12B:
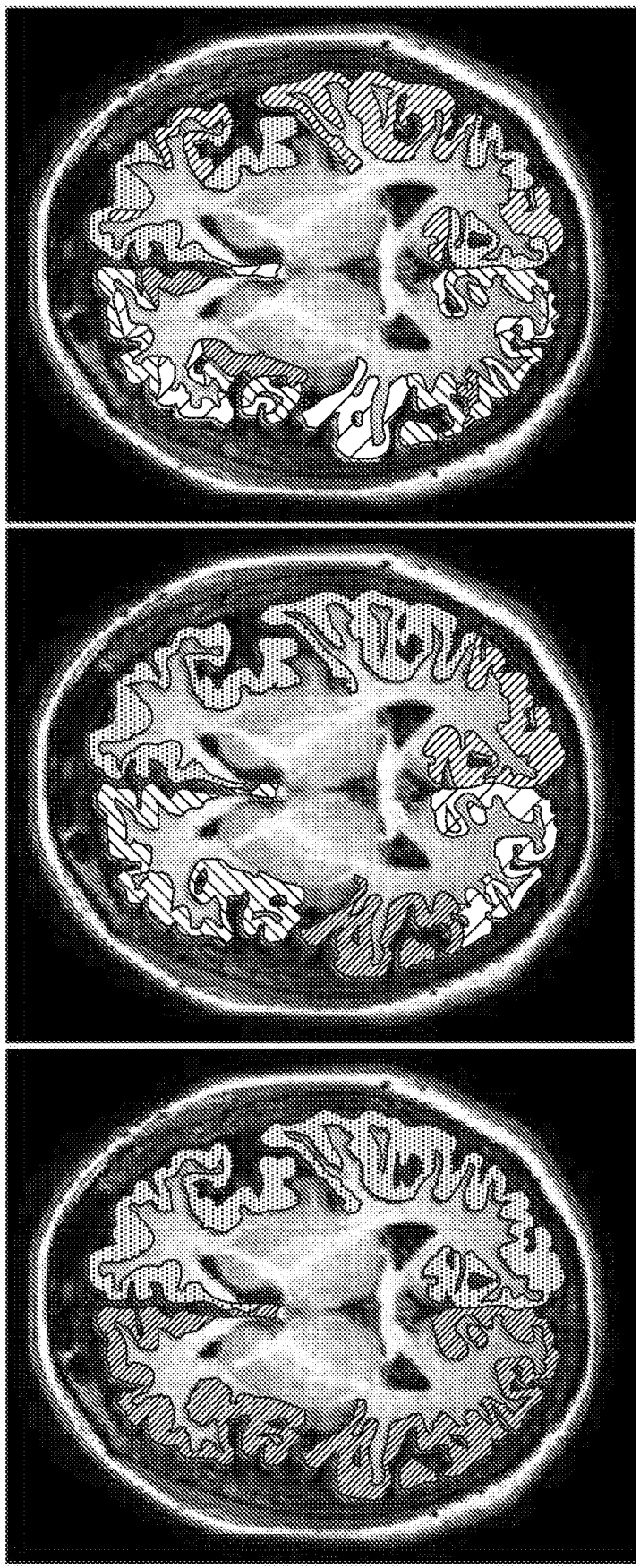
FIG. 12b shows the hierarchical levels of FIG. 12a illustrated in 2D images of the brain (first to third hierarchical levels shown left to right).

For comparison, FIG. 12b is an alternative, more conventional representation of the hierarchical structure of the brain. In particular, FIG. 12b shows three sections or views of the brain. The left-most region has been coloured to indicate the highest level of the anatomical hierarchy (the split into left and right hemispheres); the central images shows the lobar separation for each hemisphere; while the right image of FIG. 12b shows the parcellation within each lobe of each hemisphere. The rightmost image of FIG. 12b has been coloured to try to reflect the anatomical hierarchical relationships, however these hierarchical relationships are much more readily apparent using the spatial representation of FIG. 12a. Furthermore, the image data of FIG. 12b generally indicate only a single plane, and hence it is rather difficult to present the original three-dimensional measurement data in such images.

As discussed above, the 2D data set produced by the present approach allows for a representation of the physical measurement data. These measurement data may represent quantitative values, such as volumes density, uptake mass, and/or or comparative values, such as percentile, ratio, etc. The measurement data can be considered as biomarkers which provide information of potential clinical relevance to a practitioner. In some cases the measurement data are presented using a continuous range of values, in other cases the values may be quantised to a discrete set of ranges. One possibility is that the measurement data are thresholded, such that values for an element below the threshold might be shown as one colour, while values above the threshold might be shown as a different, contrasting colour. This approach might be used, for example, where the physical measurement data are determined from two or more image data sets acquired at different times, and a region is highlighted with a particular colour if the (absolute) change in the measurement value between the two image data sets exceeds a predetermined threshold. In some cases, the colour (or other property) used to represent a given element may indicate the value of the physical measurement for that element with respect to a threshold, e.g., green for normal values, red for truly abnormal values and orange for values borderline with abnormality. The physical measurement data may be scaled (and/or the representational axis for these values may be scaled) as appropriate, such as according to a linear, squeezed, log-transformed, scale etc. The choice of scaling may be modified or adapted so as to enhance specific aspects of a particular data set, e.g. to highlight small but significant differences.

Figure 13:
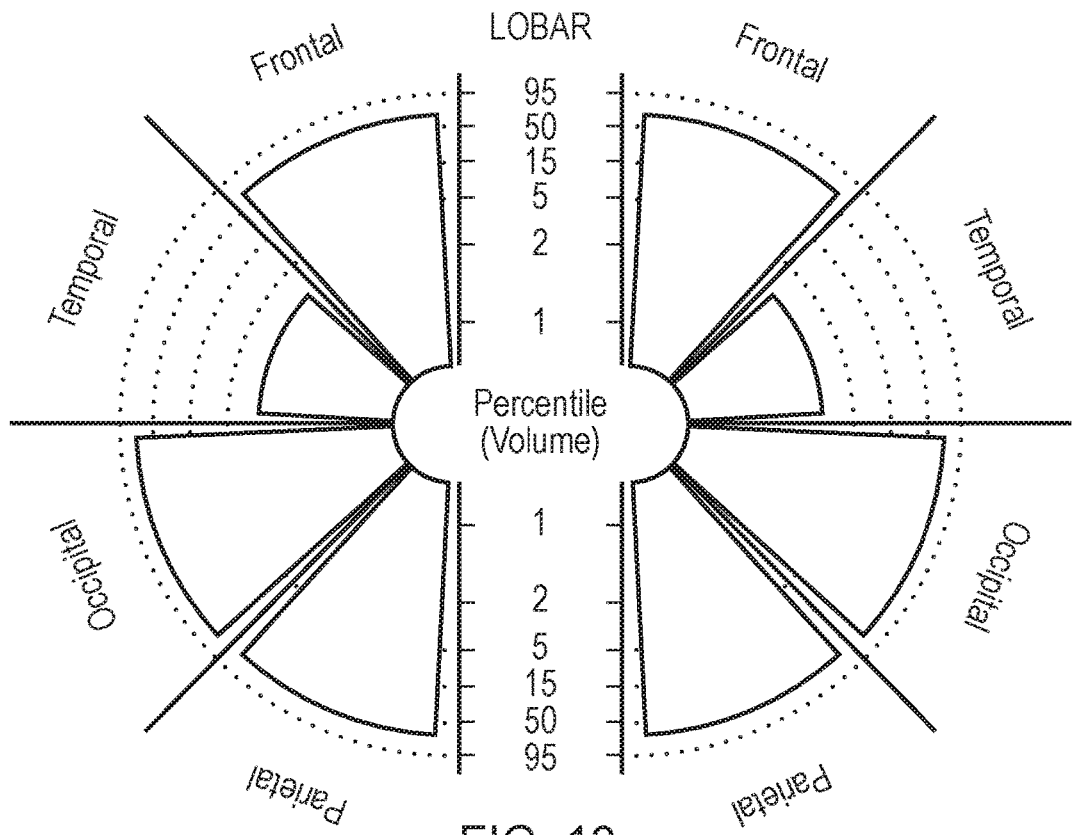
FIG. 13 illustrates a two-dimensional representation as described herein using bar plots to represent values of the physical measurement data.
Figure 14:
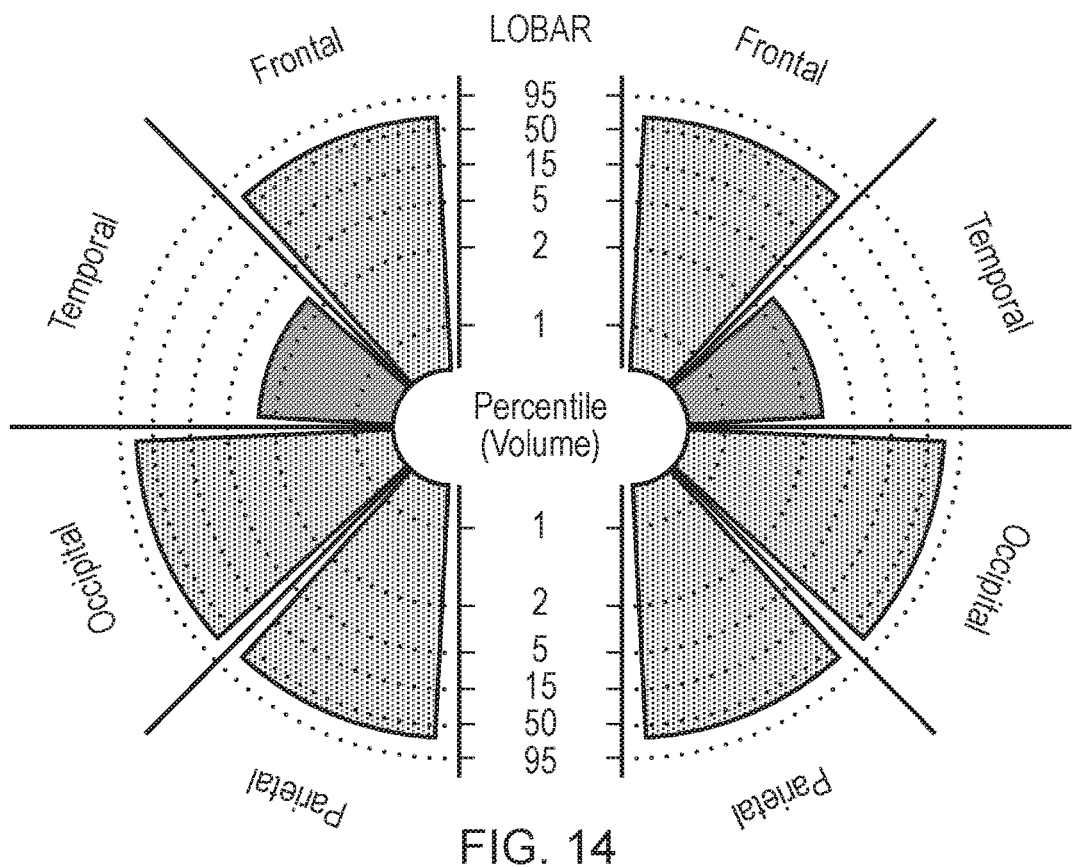
FIG. 14 illustrates a two-dimensional representation as described herein using both bar plots and colour to represent values of the physical measurement data.
Figure 15:
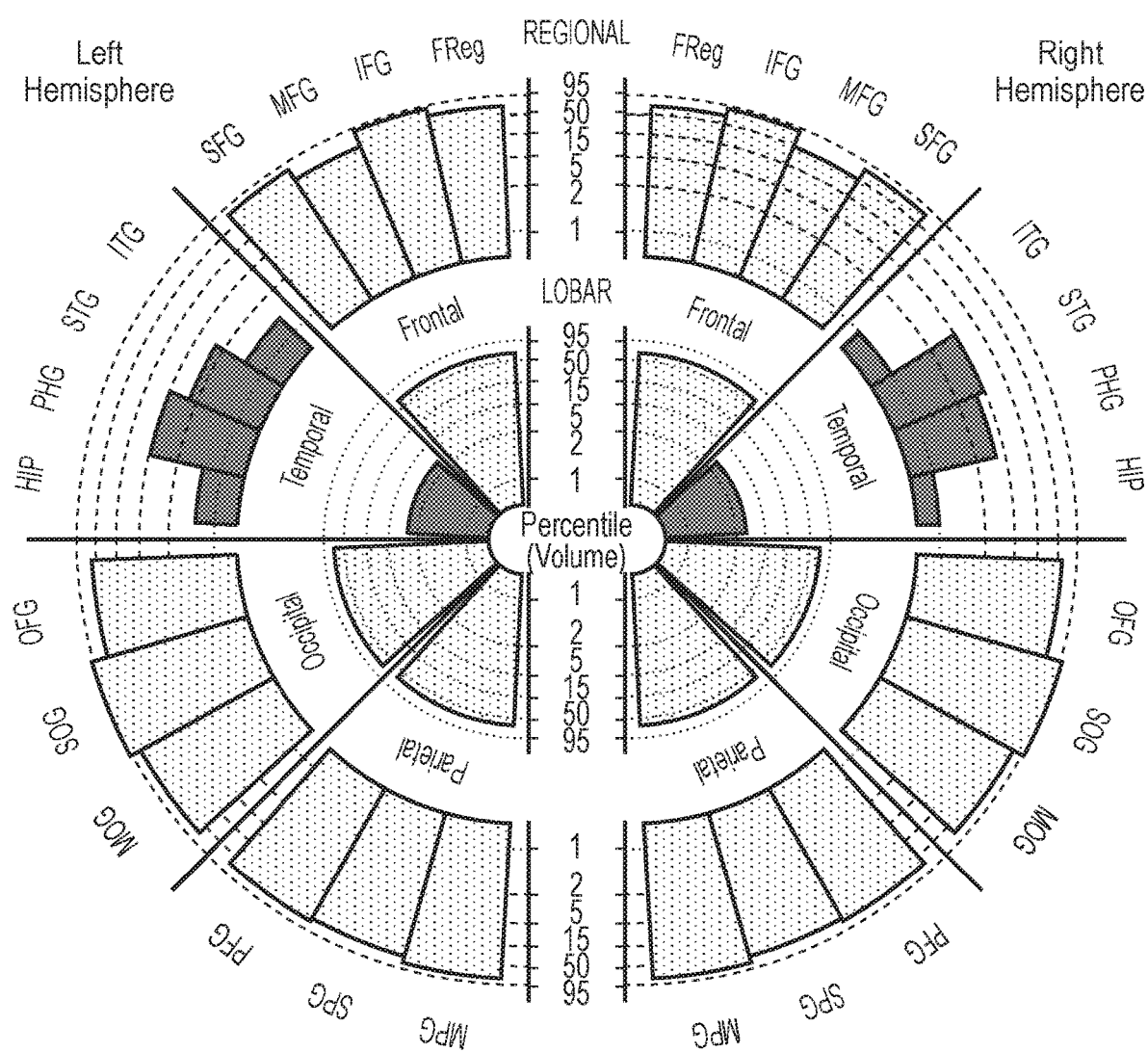
FIG. 15 illustrates a two-dimensional representation as described herein using bar plots, colour, and hierarchical rings to represent values of the physical measurement data.

FIGS. 13, 14 and 15 show some further variations on the plots described above. Each of these plots is based on the same use of polar coordinates in which the radial direction corresponds to descent through levels of the hierarchy (although only one level of the hierarchy is shown in FIGS. 13 and 14), and the angular or azimuthal direction corresponds to a spatial path through a given hierarchical level. This choice of coordinates generally gives rise to the circular (or elliptical or oval) plots of FIGS. 13, 14 and 15. In addition, a central split has been provided in these diagrams to emphasise the left-right symmetry. In particular, the left-hand portion of each of these three Figures represents a spatial path through the left hemisphere of the brain, while the right-hand portion represents a corresponding (e.g. mirror image) path through the right hemisphere of the brain. Accordingly, this representation preserves the left-right split of the original 3-D measurement data.

In FIGS. 13, 14 and 15, rather than using colour to represent the physical measurement data (and the values thereof), this is done in the form of a bar plot, whereby the size of a bar (or analogous shape) corresponds to the value of the physical measurement data for that element. Thus the plot of FIG. 13 is produced by estimating grey matter volume for each of the defined volumes corresponding to elements of the hierarchical structure, and then deriving an estimate of the corresponding age-matched percentile for each volume (element) in a single level of the hierarchical structure. This age-matched percentile is then indicated in FIG. 13 by the radial extent of the bar or sector used to denote that element. This particular representation uses a log-transformed axis to represent the profiles, as indicated by the scale provided in the split between the left and right portions of the diagram. Such a log-transformed axis can be used to enhance the display of elements/areas that fall below an acceptable level. For example, 50% or above corresponds to a normal organ, whereas below 50% may indicate an underlying condition or illness. In this Figure, more stress or emphasis is placed on lower percentile elements by the relative sizing of the bars, e.g., a smaller height (or radial depth). This can help to immediately alert a medical practitioner to an underlying condition.

FIG. 14 is a representation of the same data as shown in FIG. 13, but the bar plot has been supplemented by colour. In particular, a green colouring is used to denote the regions for which the age-matched percentile is relatively normal, i.e. the grey matter volume is at an expected or typical level for these regions, whereas a brown colouring is used to denote regions for which the age-matched percentile is relatively abnormal, i.e. the grey matter volume is significantly below the expected or typical level for these regions. In the plot of FIG. 14, it can be seen that for both left and right hemispheres, the temporal region (lobe) has such a low level of grey matter.

Note that in the plot of FIG. 14, the colour is used to denote the same physical measurement (grey matter volume) as the size of the bars or sectors. In this sense, the colour is used to reinforce the impression given by the size of the bars, and in particular to highlight any bar which is significantly small in size. However, in other situations, the bar sizes and the colour might represent different physical measurements. For example, the bar size might still indicate the grey matter volume, as for FIGS. 13 and 14, but the colour might represent (for example) some measurement of blood flow into the relevant brain region, or the concentration of certain chemicals in the relevant brain regions. In this case, a comparison between the bar size and the colour would allow an initial impression to be formed as to whether there is any correlation between the grey matter volume and the other parameter(s) being measured (such as blood flow, chemical concentration, etc.).

While FIGS. 13 and 14 illustrate just a single hierarchical level, the use of bar sizings is compatible with a representation of multiple hierarchical levels, as shown in FIG. 15. In particular, the inner ring of FIG. 15 corresponds to the plot of FIG. 14, but this is now supplemented by an outer ring representing the next lower level of the anatomical hierarchy. Again, in this outer ring, each element is represented by a bar or sector which is sized to represent the grey matter volume (as an age-matched percentile), and the bars are also coloured to emphasise any particular anomalies. The radial axis in FIG. 15 therefore serves two purposes—within a single ring (intra-level), it is used to denote the physical measurement value (according to the bar sizes), whereas between rings (inter-level) it is used to denote the different levels of the anatomical hierarchical structure. This double use of the radial axis does not cause confusion, because the spacing between the rings is chosen to be larger than any bar size representation of an individual element.

FIG. 15 therefore conveys additional information to the medical practitioner regarding the physical measurement data (compared with FIGS. 13 and 14). Thus looking at the inner right, it is clear that the temporal lobe of both hemispheres has a much lower percentage reading than the other lobes of that hierarchical level. If we now look at the outer ring, representing subordinate elements, the medical practitioner can readily obtain further information (assisted by the clear spatial relationship in FIG. 15 between the representations of the temporal lobe and its subordinate elements). For example, it can be seen that within the temporal lobe, the hippocampus (HIP) and inferior temporal gyrus (ITG) contribute an especially low percentage of grey matter—which is emphasised in FIG. 15 by the reddish-brown colouring of these two subordinate elements—with the situation being particularly acute in the temporal lobe of the right hemisphere. It will be appreciated that FIG. 15 provides the medical practitioner with an important and useful tool for understanding, interpreting, and utilising the underlying physical measurement data.

FIGS. 16, 17A, 17B, 18, 19 and 20 show further representations of physical measurement data for the brain using the approach described herein, but with a different format from FIG. 15. Thus these Figures again represent two hierarchical levels, but in this case the lower hierarchical level corresponds to the inner ring (rather than to the outer ring as for FIG. 15). Furthermore, the outer ring is transformed (in homotopic fashion) to form two lines of elements, one on each side of the inner ring. Each element within these two lines corresponds to a larger volume of the brain formed from multiple smaller regions shown in the lower level of the hierarchy (the inner ring). It will be appreciated that this representation emphasises the left-right structure (symmetry) of the brain, i.e. the left and right lines of elements correspond to the left and right sides of the brain respectively.

Figure 16:
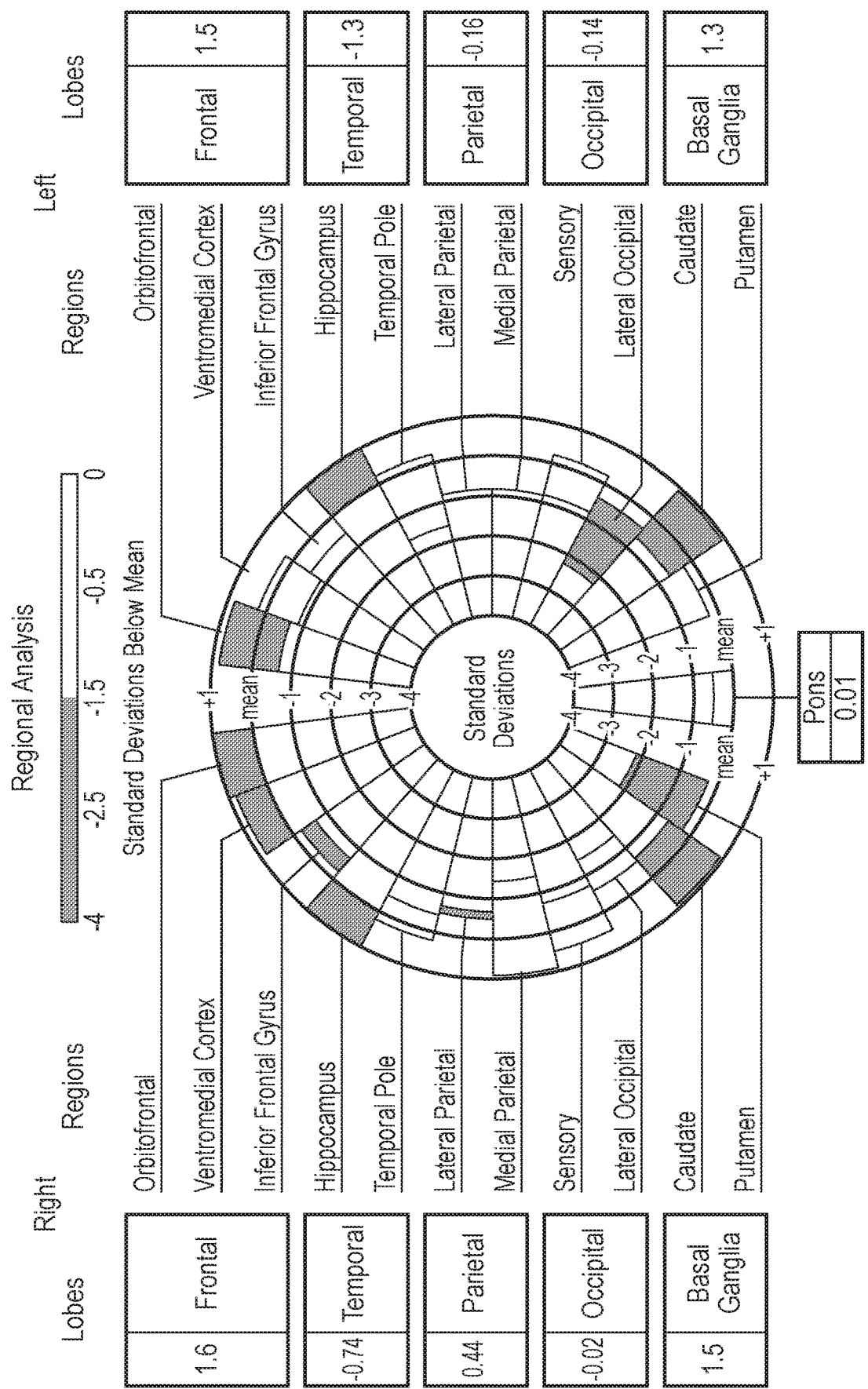
FIG. 16 illustrates a two-dimensional representation as described herein using bar plots and colour to represent values of the physical measurement data, including a temporal change in such values.

FIG. 16 illustrates how such a representation can be used to denote a measured physical property, e.g. volume, concentration of a chemical, neural activity etc (as previously indicated, such a measurement may represent directly acquired data, or data generated from such acquired data, etc). The measurement data is determined as a number of standard deviations from a mean, the mean and standard deviation being derived from population data, which may be matched according to appropriate factors, e.g. age, gender, medical diagnosis, etc. For the outer set of elements, configured in the two lines on either side of the display and representing the higher level of the hierarchical structure, the standard deviation is colour-coded according to the scale provided by the colour bar at the top of the chart (any value above the mean is colour-coded green, the same as the mean itself). Each element in the higher level of the hierarchical structure is then provided with a box coloured according to this colour code. Each box is further provided with the relevant numerical value in standard deviations corresponding to the colour coding (and also the name of the corresponding anatomical region).

For the inner circular representation, the radial length of each bar or segment shows the change between two measurements at different times. In particular, if a portion of a bar is shown in red, this indicates a decrease in the measured value by an amount represented by the size of the red portion (i.e. a large red portion indicates a large decrease). Conversely, a green portion indicates an increase in the measured value by an amount represented by the size of the green portion. In this way, the display of FIG. 16 is also able to provide information about temporal changes in the values of the physical measurements.

Figure 17A:
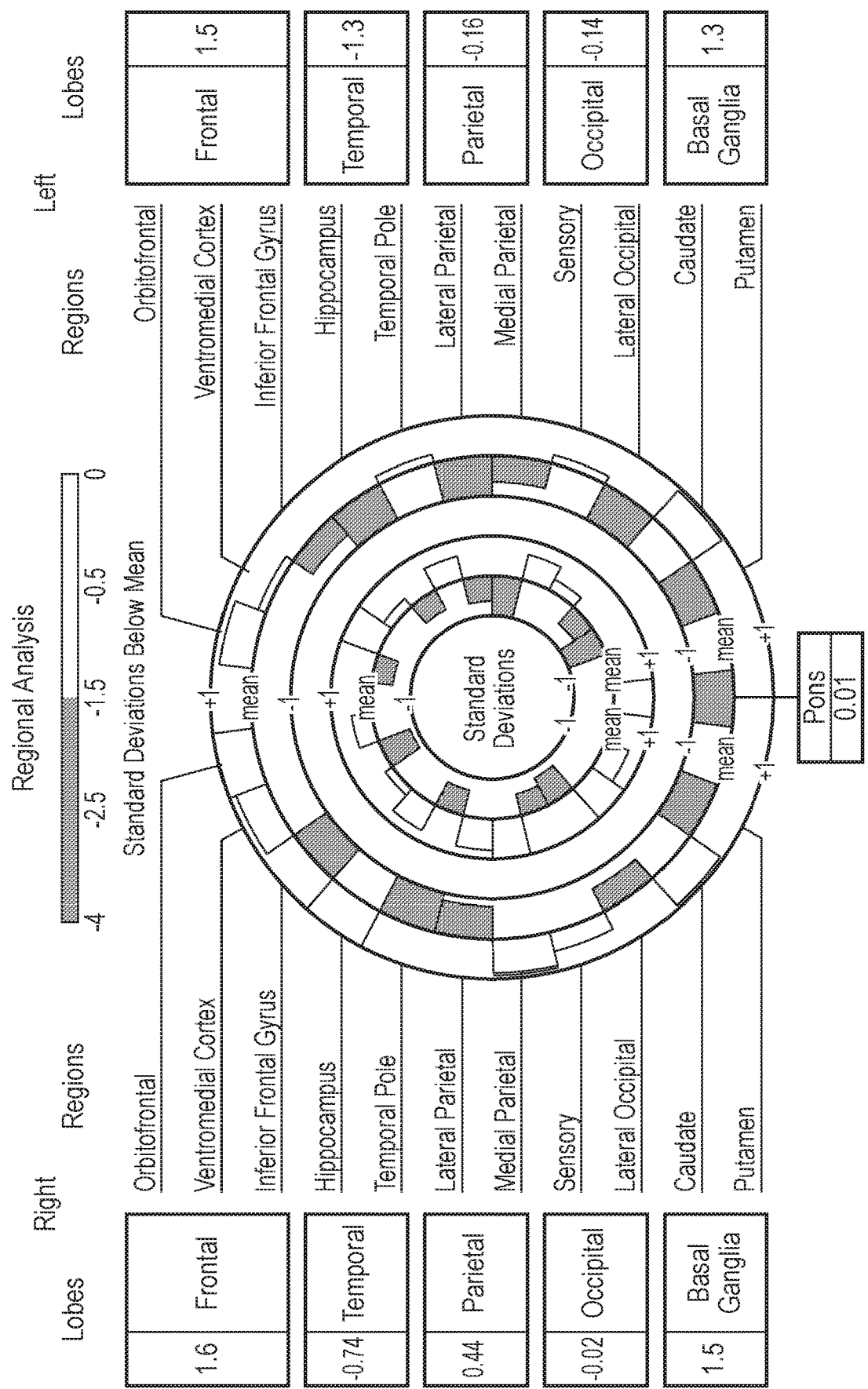
FIGS. 17A and 17B illustrate two-dimensional representations as described herein using bar plots and colour to represent multiple (e.g. two) values of the physical measurement data for each anatomical element in the lowest level of the hierarchy.
Figure 17B:
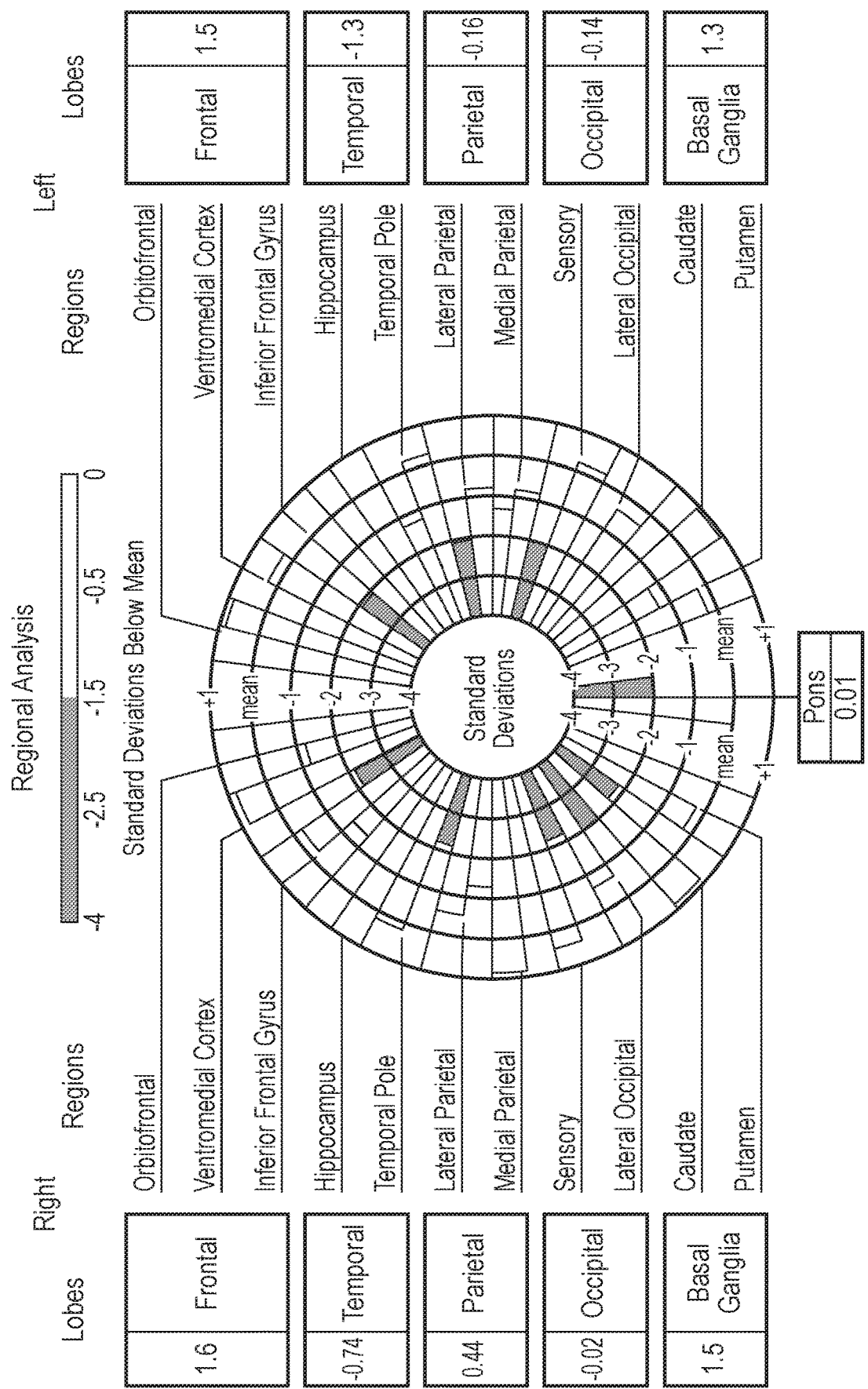

FIGS. 17A and 17B share the same overall format as FIG. 16, and again represent data values based on standard deviations from the mean. FIG. 17A shows two different sets of physical measurement data displayed using two concentric rings, each ring denoting the mean for that measurement. Each element has an associated bar to indicate the measured number of standard deviations from the mean for that element—a positive displacement being shown in green, and a negative displacement being shown in orange-brown. In this case, the two different measurements (corresponding to the inner and outer rings) may respectively represent measurements of the same physical parameter at two different times (as for FIG. 16) or measurements of two different physical parameters (such as Volume and PET Tracer Uptake).

FIG. 17B is analogous to FIG. 17A in showing two related measurements for each element, e.g. measurements of the same physical parameter at two different times or measurements of two different physical parameters for that element. However, rather than the two related measurements being shown in respective rings (as for FIG. 17A), in this case the two related measurements are shown side by side (in an azimuthal orientation) by bar segments—more analogous to the approach of FIG. 16.

Figure 18:
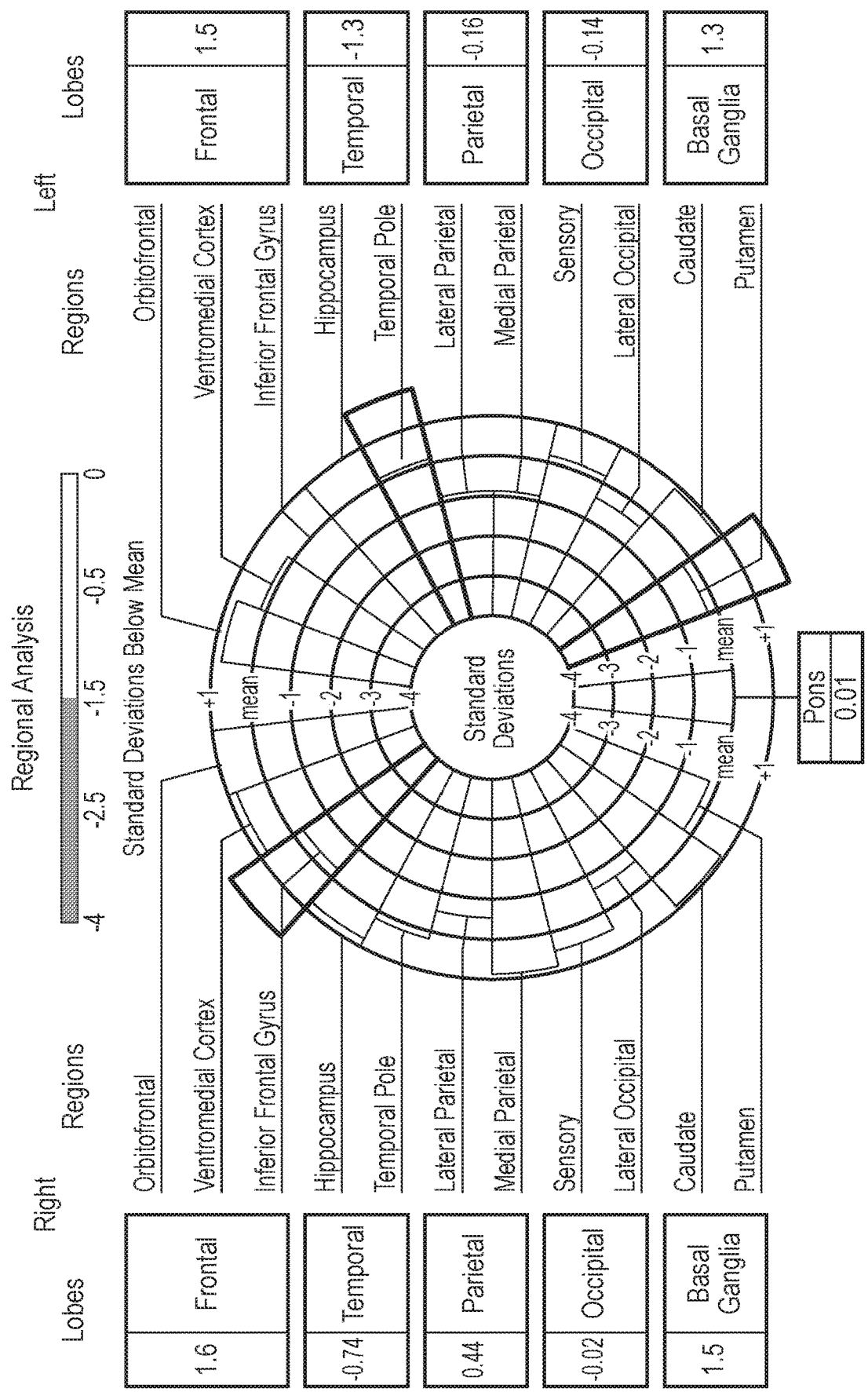
FIG. 18 illustrates a two-dimensional representation as described herein using bar plots and colour to represent values of the physical measurement data, including additional markings to draw attention to certain anatomical elements in the lowest level of the hierarchy.

FIG. 18 shows another display analogous to FIGS. 16 and 17B. In this diagram, the bars for selected elements in the lower level of the hierarchy have been high-lighted by blue markers. Such markers may be used by the system and/or user to draw attention to a particular region of interest. For example, the system may mark certain elements that have an anomalous value, or a use may mark certain segments that are of particular interest (e.g. because for a given subject they have given an anomalous result in a previous investigation).

Figure 19:
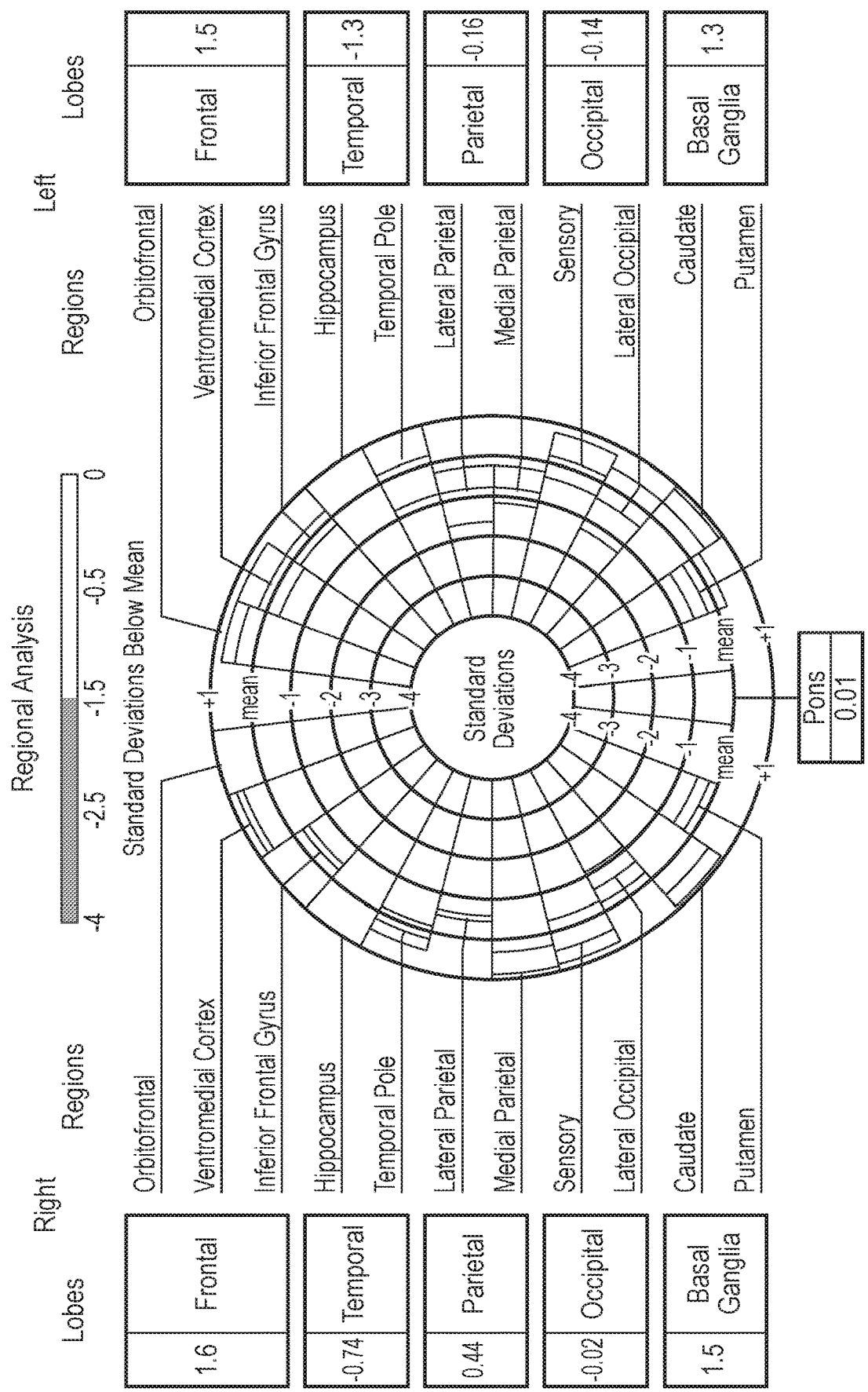
FIG. 19 illustrates a two-dimensional representation as described herein using bar plots and colour to represent values of the physical measurement data, including an indication of the errors associated with such values.

The skilled person will be aware of various other ways of marking or providing information associated with the data bars corresponding to respective structural elements. For example, as shown in FIG. 19, each data bar might include some form of radial error bar indicating the uncertainty associated with a given physical measurement. In FIG. 19 these error bars are represented by the blue blocks superimposed on the underlying data bars, however, other implementations may use lines, arrows, etc to represent the size of error.

Figure 20:
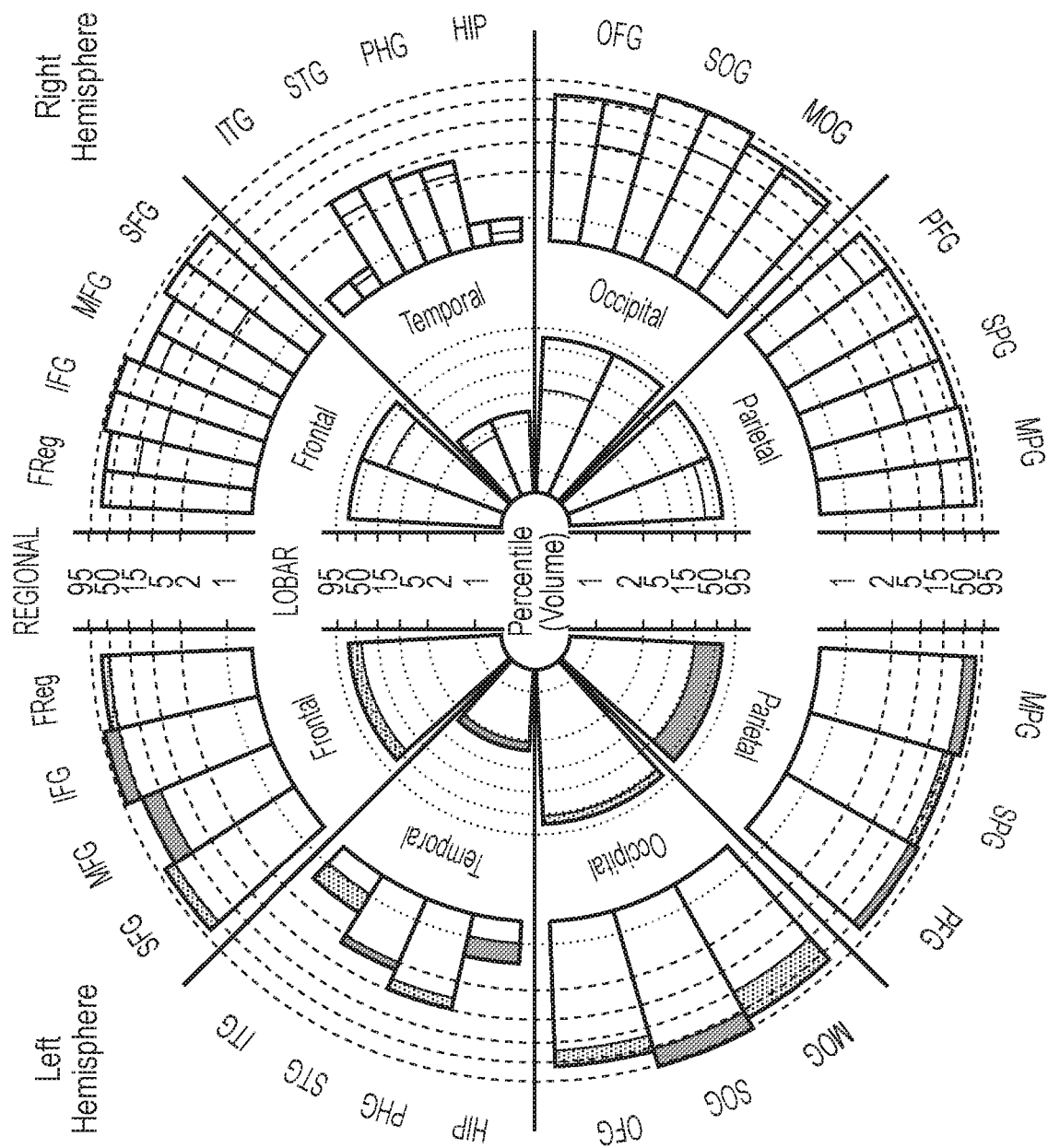
FIG. 20 illustrates a two-dimensional representation akin to FIG. 15 using bar plots, colour, and hierarchical rings to represent values of the physical measurement data. This diagram also depicts a temporal change in such values (left) and two values of the physical measurement data for each anatomical element in the lowest level of the hierarchy (right).

FIG. 20 shows a display that follows FIG. 15 in radial configuration of the different hierarchical levels, but includes some of the additional physical measurement data discussed above. In particular, the left-hand portion of FIG. 20 shows a change with time for each data element, analogous to FIG. 16, with the red and green sections indicating a decrease or increase respectively. The right-hand portion of FIG. 20 shows two data values for each element represented by side-by-side bars, analogous to FIG. 17B. (These two adjacent bars could be provided with different colouring, as for FIG. 17B, if so desired).

The approach described herein is not limited to representing any particular physical measurement data or value, but rather can be used to represent values of any appropriate physical measurements (whether directly measured, or derived from such measurements), wherein the representation seeks to capture the variation in the parameter(s) of physical measurements across the three-dimensional volume of a biological organ. A segmentation procedure may be utilised to select the physical measurement data corresponding to the biological organ of interest.

The 2D representation of the physical measurements generated herein retains spatial relationships (to a certain degree) by defining one axis of the representation as a spatial path through the organ. This spatial path will generally be continuous, such that adjacent regions in the organ map to adjacent regions in the representation. However, the path may be arranged to have one or more discontinuities if this is considered to provide a more meaningful ordering—e.g. to help provide a symmetric arrangement of left and right hemispheres of the brain, if so desired, or to arrange for each element in a given hierarchical level to appear only once. (Note that arranging for each element in a given hierarchical level to appear only once could also be achieved, for example, by disregarding any additional intersections between a continuous spatial path and the 3D volume corresponding to the element). The 2D representation uses a second axis to reflect the hierarchical anatomical or functional structure of the organ. Overall, the 2D representation generated herein is easy to display to a medical practitioner, e.g. on a computer screen, on a printed chart, etc., and provides clinically relevant information in a manner that supports quick understanding by a medical practitioner (at least in part because of the clear relationship between the representation and the underlying physical reality of the biological organ of interest. In addition, it will be understood that the various 2D representations illustrated herein are provided by way of example only. The skilled person will appreciate that the features of such 2D representations can be modified, updated, interchanged, etc, as appropriate, depending upon the circumstances of any given implementation.

In some implementations, when the two-dimensional representation is displayed, e.g. on a computer screen, the medical practitioner can interact with the two-dimensional representation. For example, the user/medical practitioner may be able to move an input device (e.g., mouse cursor) over the 2-D representation of the organ. This might trigger a pop-up display of, or otherwise permit access to, the actual physical measurement data (or other relevant information, e.g., historical averages, or the raw 3-D data image data, etc.) for the element selected by the cursor (or corresponding to the current position of the cursor). In some implementations, the two-dimensional representation may comprise a number of physical measurement data for each element, but one parameter (or a subset of parameters) is presented in an individual display. When selecting a particular element, the user may be able to access these additional physical measurement data (or switch the display such that a different parameter is used as the basis of the display).

Figure 21:
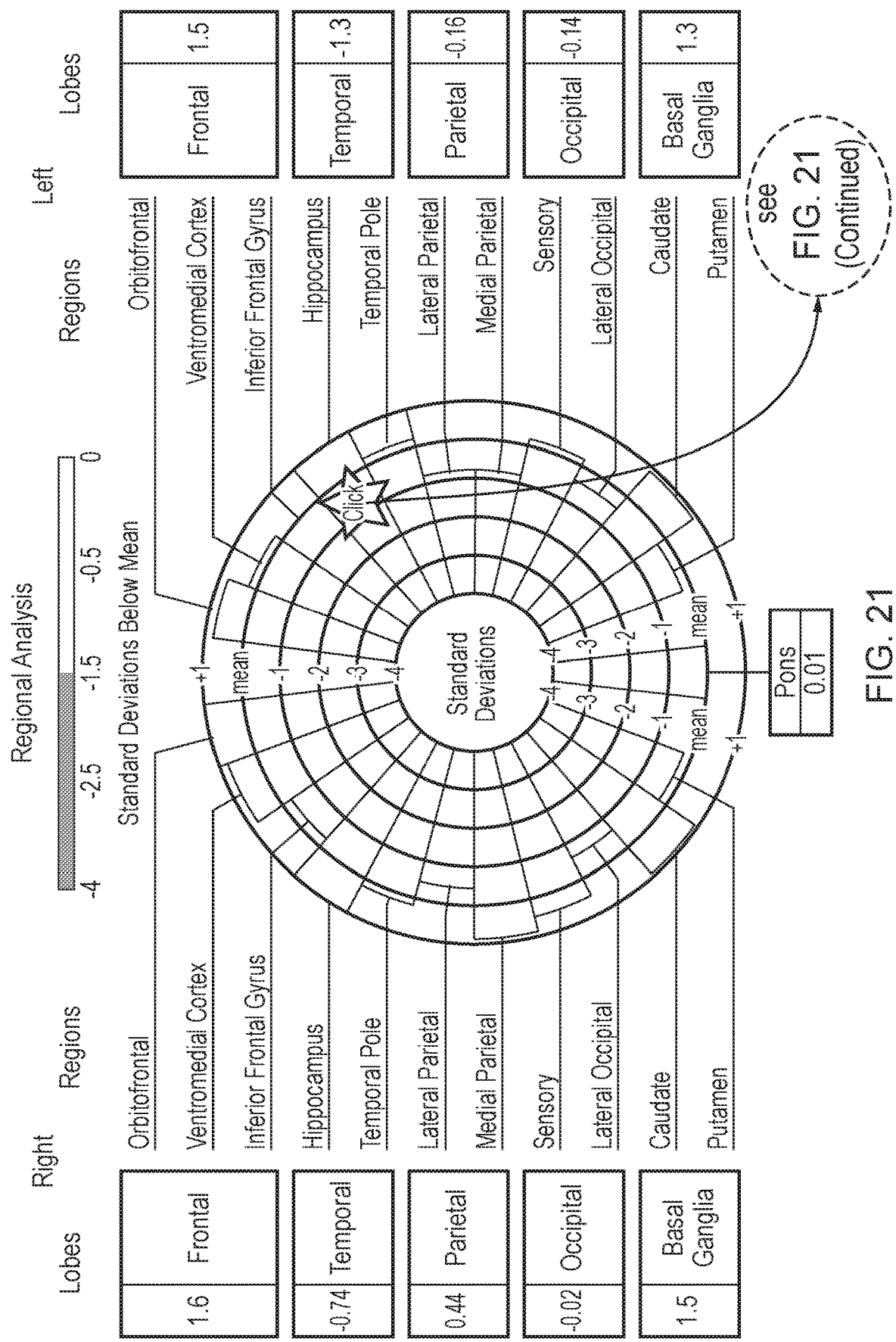
FIG. 21 illustrates a two-dimensional representation as described herein using bar plots and colour to represent values of the physical measurement data, and further illustrates how a user may interact with an element corresponding to a given anatomical structure (e.g. by clicking with a mouse) to access a display of additional information relating to such anatomical structure.
Figure 21:
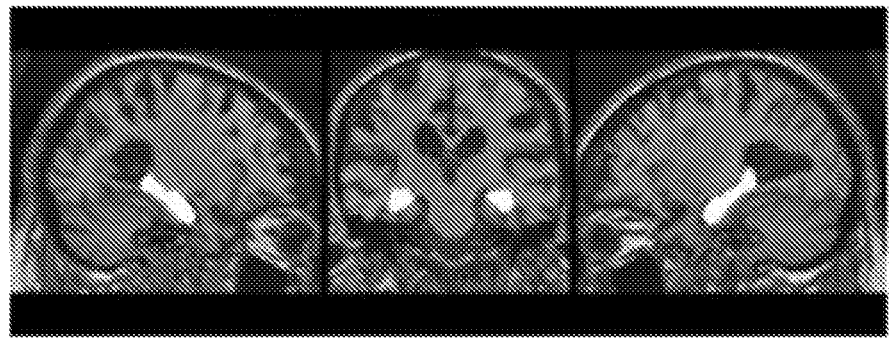
Figure 21:
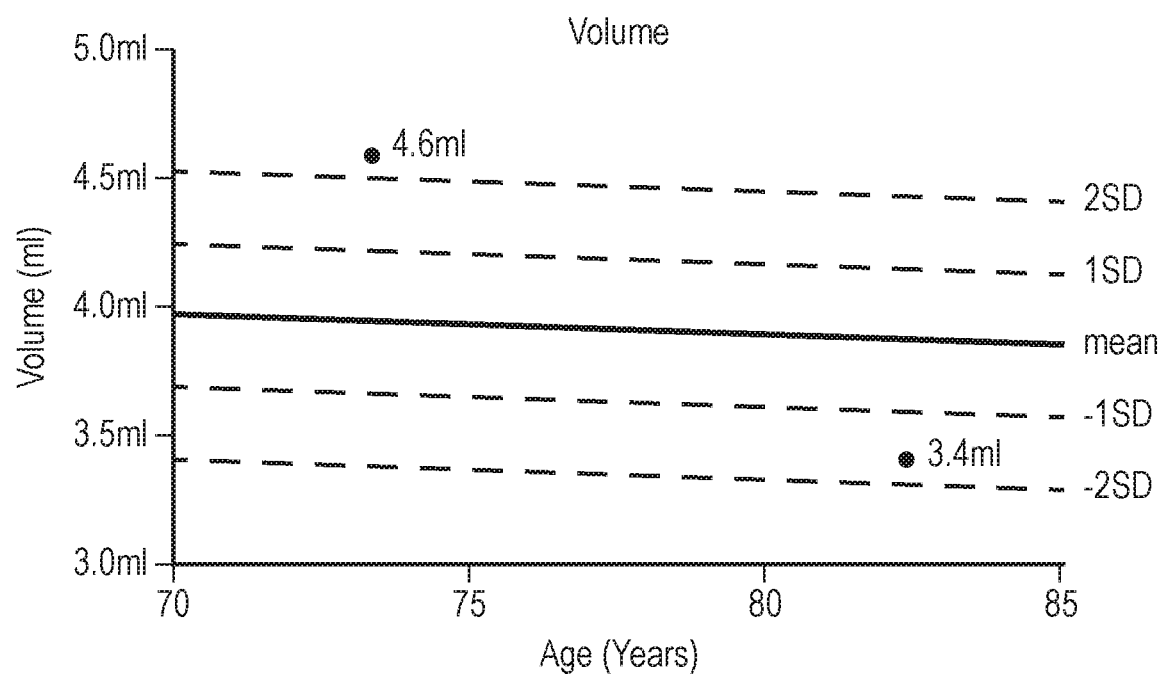
Figure 21:
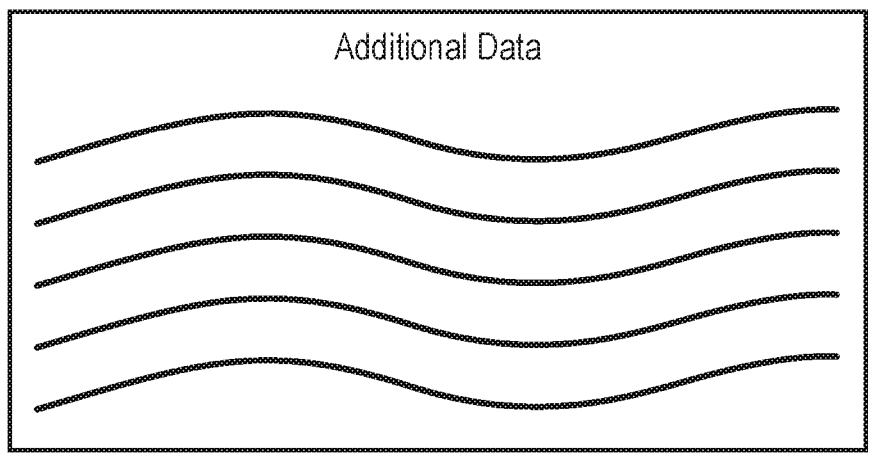

One example of such interaction is illustrated in FIG. 21, in which a 2-D representation as described above is shown in the left-hand portion of the diagram. A user is assumed to select (e.g. click on) the particular data segment corresponding to the (left) hippocampus. This may then bring up the screen (window) shown in the right-hand portion of the diagram, which provides three components. The top component presents three views of the hippocampus (axial, coronal, and sagittal) derived from appropriate imaging data. The middle component shows a plot of the distribution of volume for the left hippocampus with age for a suitable population, with the mean and various standard deviation levels flagged. This plot includes the location of the measured value for the left hippocampus currently represented in the left-hand portion of FIG. 21, namely a volume of 4.6 and an age of approximately 73. The lower right portion may be used to provide further relevant information (FIG. 21 just shows a dummy graph in this region).

Figure 2:
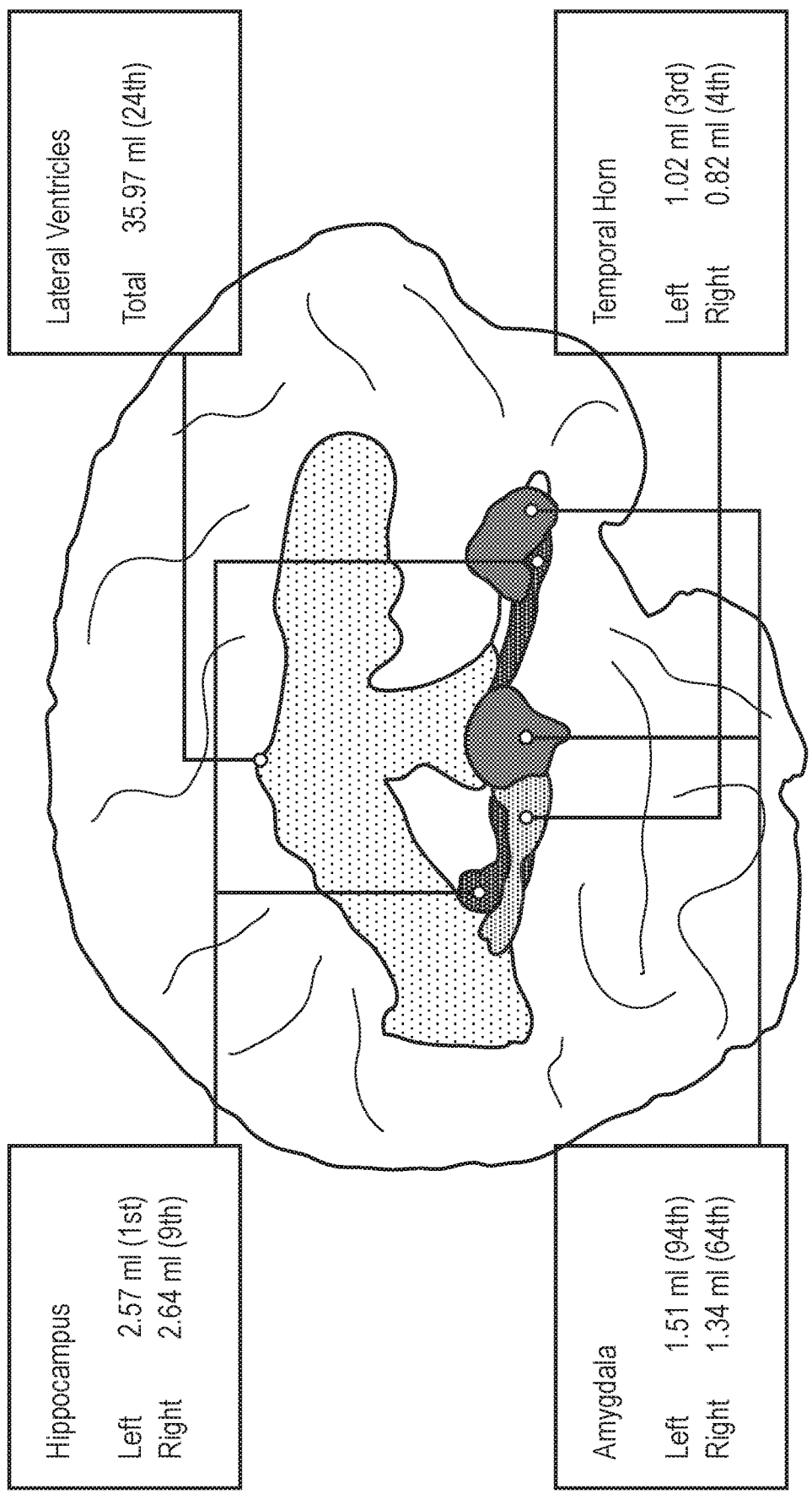
FIG. 2 is a known presentation of a view showing different regions of the brain.
Figure 3:
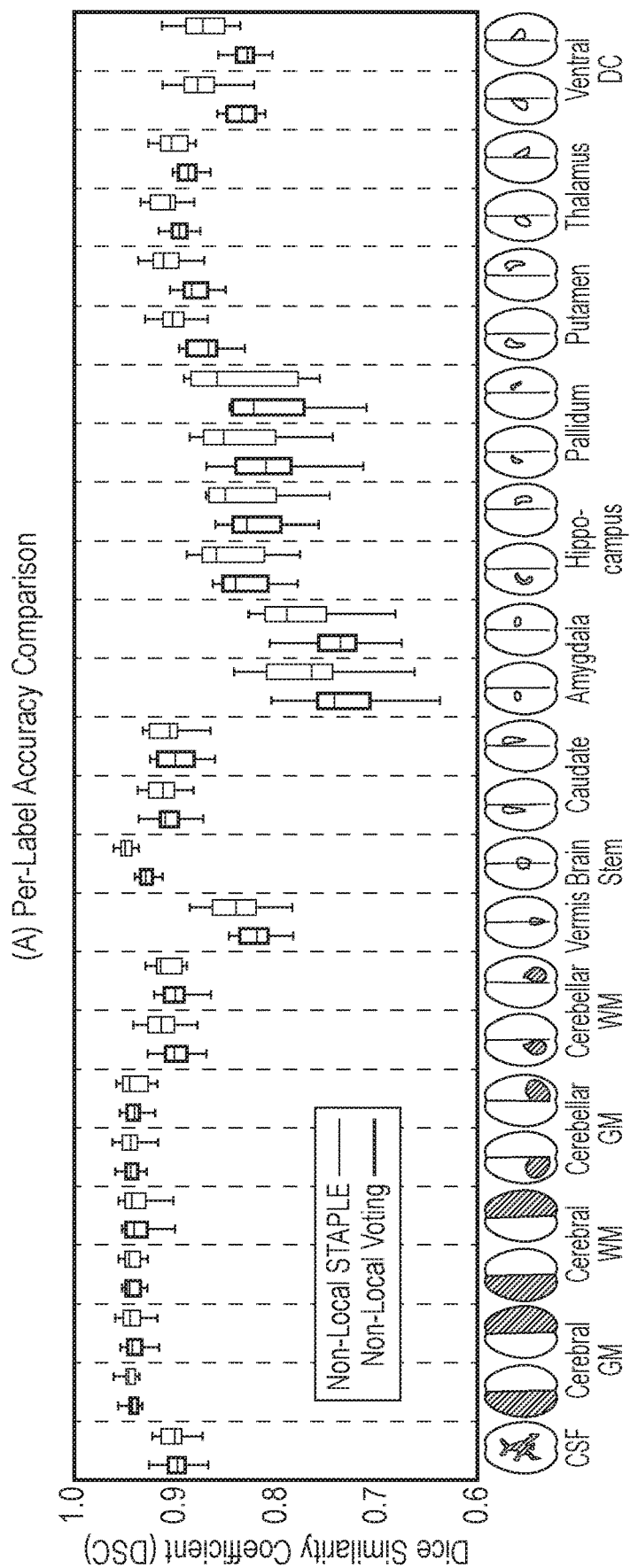
FIG. 3 is a known presentation showing experimental results for different regions of the brain.

A user may also be presented with various control facilities for altering the display of the 2-D data representation. For example, the user might be able to hide lower levels of the hierarchy (e.g. to simplify the display); in some cases clicking on a given element may alternately hide and then display the branch descending from this particular element. A user may also be able to change the format of the display (such as between the different presentations of FIGS. 10, 11, 12, 13, 14 and 15), or to adjust the scaling of the axes, threshold levels, colour scale, and so on. The user may also be provided with an additional (simultaneous) display, such as the view of FIG. 2, which shows an image of the biological organ of interest. There may be a degree of linking between such an image and the plots described herein. For example, if a user selects an element of the plot of one of FIGS. 10-15, this may highlight the corresponding region within the view of FIG. 2 (or vice versa).

In other examples, the user may interact with the 2D representation by defining an alternative spatial path. In such a case, the method of FIG. 5 may be repeated to transform the 3D physical measurement data in accordance with the new spatial path (or alternatively the 2D data representation could be transformed directly to reflect the new spatial path. The new spatial path may be defined by the user one element at a time or, alternatively, may be selected from a pre-configured set of spatial paths. For example, each spatial path may be optimally chosen for a certain pathological condition and, when the user choses a new spatial path, the 2D representation is altered accordingly.

Figure 22:
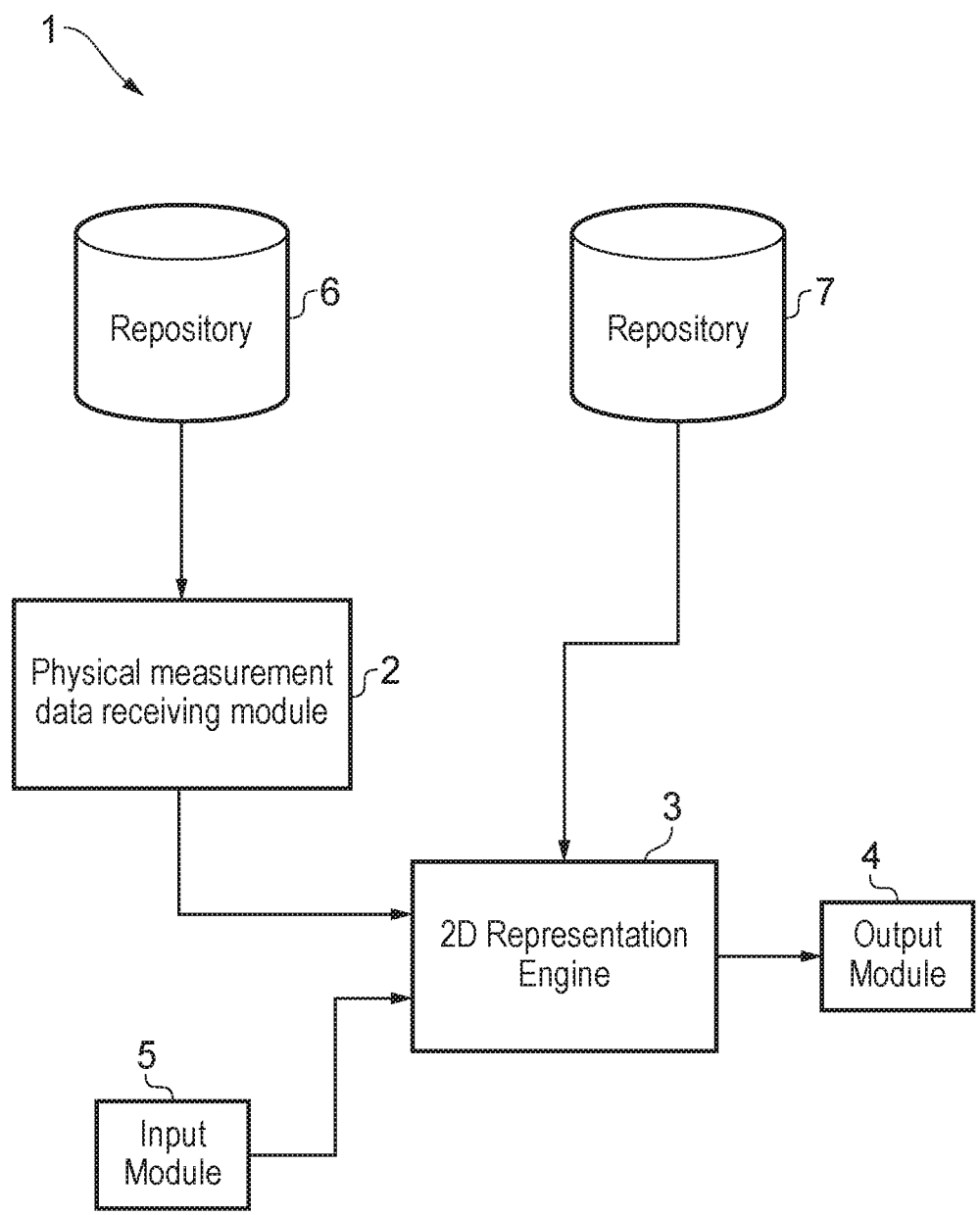
FIG. 22 schematically illustrates a system for generating a two-dimensional representation as described herein.

An example of a computer-implemented system which may be used for performing the method described herein is shown in FIG. 22. The system 1 comprises a physical measurement data receiving module 2, a two-dimensional (2D) representation engine 3, an output module 4, and input module 5, a first repository 6 and a second repository 7. The physical measurement data receiving module 2 is configured to receive three-dimensional physical measurement data of the biological organ, e.g. from a remote repository 6 or other database.

Alternatively (or additionally), the 3D data is obtained from a measurement apparatus (not shown in FIG. 22), such as an MRI or CT device, or other measurement apparatus, potentially in real-time, i.e. while the subject is still undergoing the image acquisition process, or some other clinical procedure which involves such physical measurements (or immediately thereafter). In some cases, part or all of system 1 may be incorporated or integrated into such a measurement apparatus (e.g. MRI device, etc.).

The three-dimensional data is passed to the 2D representation engine 3, which is configured to generate the two-dimensional representation or data set. For example, the 2D representation engine 3 may be configured to perform the method steps S2 to S6 described above, such as illustrated in FIG. 5. The 2D representation engine may be linked to a second repository 7 which stores hierarchical models and/or pre-defined spatial paths corresponding to generic organs for use in this transformation. The second repository may be linked or form part of the first depository, or may be integrated into the 2D representation engine 3 itself. The 2D representation engine 3 is linked to an input module 5 to receive an input from a user of the system 1. The input module (which may comprise a keyboard, display screen with mouse, etc.) can be used to control the registration process, for example by identifying the 3-D data set(s), hierarchical model, and spatial path(s) to use. In some cases, the spatial paths might be entered directly by a user via input module 5, rather than being retrieved from a repository 7.

The two-dimensional representation generated by engine 3 may be passed to the output module 4, which can be is configured to format the two-dimensional representation for display on a screen or similar device (which may form part of the output module). The two-dimensional representation may additionally (or alternatively) be saved as a data set to an appropriate location (e.g. repository 6, repository 7, or any other appropriate storage facility), e.g. for future analysis, display, etc., and/or for archival purposes. Note that the output module 4 and the input module 5 may be formed as a single input/output facility to control various aspects of the processing and display, such as described above.

The physical measurement data used by system 1 will generally be segmented or parceled to define which volume of measurement data is to be associated with which element (region) of the organ hierarchy. This segmentation may be performed within the 2D representation engine itself, or as a form of pre-processing by some other device or program (not shown in FIG. 22).

In addition, as described above, the raw (original) physical measurement data may be processed or selected before eventual display to the user. This processing and/or selection may be performed before, after, or as part of the transformation by engine 3 (or any combination therefore). For example, there may be initial pre-processing of the physical measurement data to map from initially acquired data values to calibrated and/or normalised values. These physical measurement data used for the transformation by the 2D representation engine 3, which may perform some averaging or other processing within elements at the lowest level of the hierarchy. There may be further processing when the resulting 2D data set is to be displayed to a user—for example, by selecting a subset of the various types of physical measurement data available for each location, by selecting a thresholding approach, by performing further normalisation (such as converting to age matched-percentile as for FIGS. 13, 14 and 15).

The system 1 of FIG. 22 may be implemented in hardware and or software as appropriate. For example, the physical measurement data receiving module 2, input module 5, processing engine 3 and output module 4 may be implemented by software running on a conventional computer or the like. Alternatively, various components (or any combination of them) may be formed using specialised hardware, such as application specific integrated circuits (ASIC) or field programmable gate arrays (FPGAs) provided on dedicated printed circuit boards (PCBs).

Although various implementations and embodiments have been described herein, it will be appreciated that these are presented by way of example only, and that various modifications and adaptions of such implementations will be apparent to the skilled person according to the circumstances of any given implementation. Accordingly, the present invention is not limited to the specific implementations and embodiments described herein, but rather is defined by the appended claims and their equivalents. It will be appreciated that features of the dependent claims may be combined with features of the independent claims in any appropriate combination (without limitation to the combinations explicitly identified in the claims themselves).

REFERENCES

[1] Asman, A. J., & Landman, B. A. (2013). Non-local statistical label fusion for multi-atlas segmentation. Medical Image Analysis, 17(2), 194-208.6 http://doi.org/10.1016/j.media.2012.10.002
[2] Cerqueira, M. D. (2002). Standardized Myocardial Segmentation and Nomenclature for Tomographic Imaging of the Heart: A Statement for Healthcare Professionals From the Cardiac Imaging Committee of the Council on Clinical Cardiology of the American Heart Association. Circulation, 105(4), 539-542. http://doi.org/10.1161/hc0402.102975
[3] Kim, K. W., Macfall, J. R., & Payne, M. E. (2008). Classification of whitte matter lesions on magnetic resonance imaging in the elderly. Biological Psychiatry, 64(4), 273-280. http://doi.org/10.1016/j.biopsych.2008.03.024.Classification
[4] Liu, S. X. (2009). Symmetry and asymmetry analysis and its implications to computer-aided diagnosis: A review of the literature. Journal of Biomedical Informatics, 42(6), 1056-64. http://doi.org/10.1016/j.jbi.2009.07.003
[5] Schiffmann, R., & van der Knaap, M. S. (2009). Invited article: an MRI-based approach to the diagnosis of white matter disorders. Neurology, 72(8), 750-9. http://doi.org/10.1212/01.wnl.0000343049.00540.c8
[6] Snowden, J., Neary, D., & Mann, D. (2007). Frontotemporal lobar degeneration: clinical and pathological relationships. Acta Neuropathologica, 114(1), 31-8. http://doi.org/10.1007/s00401-007-0236-3
[7] Volkau, I., Prakash, B., Ananthasubramaniam, A., Gupta, V., Aziz, A., & Nowinski, W. L. (2006). Quantitative analysis of brain asymmetry by using the divergence measure: normal-pathological brain discrimination. Academic Radiology, 13(6), 752-8. http://doi.org/10.1016/j.acra.2006.01.043
[8] Winston, G. P., Cardoso, M. J., Williams, E. J., Burdett, J. L., Bartlett, P. A., Espak, M., . . . Ourselin, S. (2013). Automated hippocampal segmentation in patients with epilepsy: available free online. Epilepsia, 54(12), 2166-73. http://doi.org/10.1111/epi.12408

The invention claimed is:

1. A computer-implemented method comprising:
receiving data comprising physical measurements of a biological organ across a three-dimensional (3D) volume, the organ having a hierarchical structure of elements with multiple levels;
transforming the physical measurement data into a two-dimensional (2D) data representation having first and second axes, wherein the first axis corresponds to location of an element along a spatial path through the three-dimensional volume based on the hierarchical structure of the organ, and the second axis corresponds to descending successive levels through said hierarchical structure; and
outputting the two-dimensional data representation to an apparatus for display, wherein the first axis is scaled in accordance with the hierarchical structure, such that a given branch of the hierarchical structure has a consistent size across all levels; and:
wherein all elements within a given branch and at a given level of the hierarchical structure have the same size;
wherein all elements correspond to a respective sub-volume of the three-dimensional (3D) volume, and all elements within a given branch and at a given level of the hierarchical structure are scaled in the 2D representation relative to one another according to the physical size of their respective sub-volumes; or
wherein all elements within a given branch and at a given level of the hierarchical structure have the same size.

2. The method of claim 1, wherein transforming includes:
providing the spatial path through the three-dimensional volume, the spatial path for a given level of a hierarchical structure passing through elements within the given level of the hierarchical structure to define an ordering for the elements within the given level, said ordering reflecting at least in part the relative positions of the elements in the three-dimensional volume.

3. The method of claim 2, wherein the same spatial path is used for each level of the hierarchical structure.

4. The method of claim 1, wherein the spatial path has a first portion through a first region of the organ, and a second portion through a second region of the organ, wherein the first and second portions of the spatial path are symmetric.

5. The method of claim 1, further comprising:
identifying a sub-volume of the three-dimensional (3D) volume corresponding to a given element in the hierarchical structure of the biological organ; and
mapping the physical measurement data within the sub-volume to a corresponding location in the 2D representation according to (i) the level in which the given element is located in the hierarchical structure, and (ii) the location of the given element along said spatial path.

6. The method of claim 5, wherein the identifying and mapping is performed for each element in the hierarchical structure.

7. The method of claim 1, wherein the two-dimensional representation is based on a polar coordinate system, wherein the first axis corresponds to the angular coordinate and the second axis corresponds to the radial coordinate; and:
wherein the hierarchical structure is represented by a series of concentric rings, and the uppermost hierarchical level is represented by the innermost ring;
wherein the two-dimension representation comprises at least an upper level and a lower level of the hierarchical structure, wherein the lower level is based on an angular coordinate corresponding to the first axis, and the upper level is located radially outside the lower level, and is based on a homotopic mapping of said angular coordinate, or is configured as a pair of linear arrangements located on opposing sides of the lower level.

8. The method of claim 1, wherein the two-dimensional representation is based on Cartesian (x-y) coordinates, wherein the first axis of the 2D representation corresponds to one of the x or y axis and the second axis of the 2D representation corresponds to the other of the x or y axis.

9. The method of claim 1, wherein all elements correspond to a respective sub-volume of the three-dimensional (3D) volume, and the method further comprising averaging the physical measurement data for an element over the respective sub-volume for that element.

10. The method of claim 1, wherein the physical measurement data corresponding to a particular element of the hierarchical structure is represented by a colour according to the value of the physical measurement data for that element or is represented by a sizing of a display element along the second axis, within one level of the hierarchy.

11. The method of claim 1, wherein the 2D representation preserves a symmetry of the biological organ.

12. The method of claim 1, wherein the biological organ is the brain.

13. The method of claim 1, wherein the physical measurement data comprises data acquired from an imaging system or other measurement system, or is derived from such data.

14. The method of claim 1, further comprising:
displaying the two-dimensional representation at the apparatus for display;
receiving an input in association with the displayed two-dimensional representation; and
modifying the two-dimensional representation in accordance with the received input.

15. A non-transitory computer readable medium comprising instructions that, when executed on a computer, cause the computer to perform the method of claim 1.

16. Apparatus configured to perform the operations of:
receiving data comprising physical measurements of a biological organ across a three-dimensional (3D) volume, the organ having a hierarchical structure of elements with multiple levels;
transforming the physical measurement data into a two-dimensional (2D) data representation having first and second axes, wherein the first axis corresponds to location of an element along a spatial path through the three-dimensional volume based on the hierarchical structure of the organ, and the second axis corresponds to descending successive levels through said hierarchical structure; and
outputting the two-dimensional data representation to an apparatus for display, wherein the first axis is scaled in accordance with the hierarchical structure, such that a given branch of the hierarchical structure has a consistent size across all levels; and:
wherein all elements within a given branch and at a given level of the hierarchical structure have the same size;
wherein all elements correspond to a respective sub-volume of the three-dimensional (3D) volume, and all elements within a given branch and at a given level of the hierarchical structure are scaled in the 2D representation relative to one another according to the physical size of their respective sub-volumes; or
wherein all elements within a given branch and at a given level of the hierarchical structure have the same size.

17. The apparatus of claim 16, wherein said apparatus comprises one or more processors and computer program instructions for execution by the one or more processors to perform said operations.

18. The apparatus of claim 16, further comprising a display apparatus for displaying the output two-dimensional representation.

19. The apparatus of claim 16, wherein the apparatus is integrated into an image acquisition system or physical measurement acquisition system.

20. A computer-implemented method comprising:
receiving data comprising physical measurements of a biological organ across a three-dimensional (3D) volume, the organ having a hierarchical structure of elements with multiple levels;
transforming the physical measurement data into a two-dimensional (2D) data representation having first and second axes, wherein the first axis corresponds to location of an element along a spatial path through the three-dimensional volume based on the hierarchical structure of the organ, and the second axis corresponds to descending successive levels through said hierarchical structure; and
outputting the two-dimensional data representation to an apparatus for display,
wherein the two-dimensional representation is based on a polar coordinate system, wherein the first axis corresponds to the angular coordinate and the second axis corresponds to the radial coordinate; and:
wherein the hierarchical structure is represented by a series of concentric rings, and the uppermost hierarchical level is represented by the innermost ring;
wherein the two-dimension representation comprises at least an upper level and a lower level of the hierarchical structure, wherein the lower level is based on an angular coordinate corresponding to the first axis, and the upper level is located radially outside the lower level, and is based on a homotopic mapping of said angular coordinate, or is configured as a pair of linear arrangements located on opposing sides of the lower level.

* * * * *